(12) United States Patent
Russo et al.

(10) Patent No.: US 10,329,268 B2
(45) Date of Patent: Jun. 25, 2019

(54) PROCESSES FOR PREPARING MEDICAMENTS FOR THE TREATMENT OF CARDIOVASCULAR DISEASES AND INTERMEDIATES FOR USE THEREIN

(71) Applicant: Bial-Portela & CA., S.A., S. Mamede do Coronado (PT)

(72) Inventors: Domenico Russo, S. Mamede do Coronado (PT); Jorge Wahnon, S. Mamede do Coronado (PT); William Maton, S. Mamede do Coronado (PT); Beat T. Weber, Zofingen (CH); Paula Jeronimo, S. Mamede do Coronado (PT); Luisa Sousa, S. Mamede do Coronado (PT); Pedro Barrocas, S. Mamede do Coronado (PT); Rita Pires, S. Mamede do Coronado (PT); Ricardo Lima, S. Mamede do Coronado (PT); Teofilo Vasconcelos, S. Mamede do Coronado (PT)

(73) Assignee: Bial-Portela & CA, S.A., S. Mamede do Coronado (PT)

( * ) Notice: Subject to any disclaimer, the term of this patent is extended or adjusted under 35 U.S.C. 154(b) by 0 days.

(21) Appl. No.: 15/021,605

(22) PCT Filed: Sep. 12, 2014

(86) PCT No.: PCT/PT2014/000061
§ 371 (c)(1),
(2) Date: Mar. 11, 2016

(87) PCT Pub. No.: WO2015/038022
PCT Pub. Date: Mar. 19, 2015

(65) Prior Publication Data
US 2016/0221981 A1   Aug. 4, 2016

(30) Foreign Application Priority Data

Sep. 13, 2013 (GB) .................................. 1316410.8
Nov. 18, 2013 (GB) .................................. 1320366.6

(51) Int. Cl.
*C07D 311/58* (2006.01)
*C07D 405/04* (2006.01)
(Continued)

(52) U.S. Cl.
CPC ............ *C07D 311/58* (2013.01); *C07C 51/41* (2013.01); *C07D 311/12* (2013.01); *C07D 311/20* (2013.01); *C07D 405/04* (2013.01)

(58) Field of Classification Search
CPC .............................. C07D 311/58; C07D 405/04
(Continued)

(56) References Cited

U.S. PATENT DOCUMENTS

| 5,376,661 A | 12/1994 | Gullaumet et al. |
| 8,293,507 B2 | 10/2012 | Savile et al. |
| 2005/0032873 A1 | 2/2005 | Hatzenbuhler et al. |

FOREIGN PATENT DOCUMENTS

| CN | 1726211 A | 1/2006 |
| CN | 101687858 A | 3/2010 |

(Continued)

OTHER PUBLICATIONS

Al Neirabeyeh, M., D. Reynaud, T. Podona, L. Ou, C. Perdicakis, G. Coudert, G. Guillaument, L. Pichat, A. Gharib and N. Sarda, "Methoxy and hydroxy derivatives of 3,4,-dihydro 3 (di-n-propylamino)-2H-1 benzopyrans: new synthesis and dopaminergic activity" Eur.J.Med.Chem., (1991), 26 (5), pp. 497-504. (Year: 1991).*
Xiao, G., B. Liang, S. Chen, T. Ou, X. Bu and M. Yan "3-Nitro-2H-chromenes as a new clas of inhibitors against Thioredoxin Reductase and Proliferation of Cancer cells" Arch. Pharm. Chem. Life Sci. (2012), 345: pp. 767-770 (Year: 2012).*
Foreign communication from a related application—Examination Report No. 1 of Australian Patent Application No. 2014319051, dated Nov. 17, 2017, 5 pages.
(Continued)

*Primary Examiner* — Matthew P Coughlin
*Assistant Examiner* — Sager Patel
(74) *Attorney, Agent, or Firm* — Conley Rose, P.C.; Rodney B. Carroll

(57) ABSTRACT

The present invention provides a compound of formula N wherein: X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group, wherein N is in the form of the individual R- and S-enantiomer or a mixture of the (R)- and (S)-enantiomer. The present invention also provides a compound of formula MA. The present invention also provides processes for preparing the above compounds, and processes involving their use. The compounds are particularly useful as intermediates in the synthesis of peripherally-selective inhibitors of dopamine-β-hydroxylase.

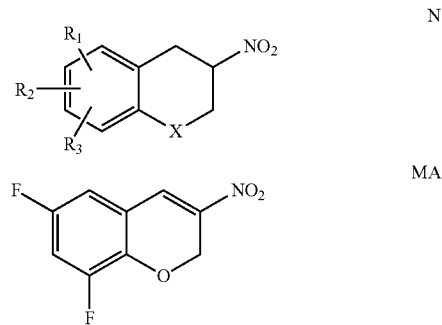

20 Claims, No Drawings

(51) Int. Cl.
    *C07D 311/12*    (2006.01)
    *C07D 311/20*    (2006.01)
    *C07C 51/41*     (2006.01)

(58) Field of Classification Search
    USPC .................................... 548/311.1; 549/404
    See application file for complete search history.

(56) References Cited

FOREIGN PATENT DOCUMENTS

| | | |
|---|---|---|
| CN | 102153533 A | 8/2011 |
| EP | 1214328 A | 6/2002 |
| FR | 2746395 A1 | 9/1997 |
| GB | 1316410.8 | 9/2013 |
| GB | 1320366.6 | 11/2013 |
| GR | 1 005 093 B1 | 1/2006 |
| JP | 2007500718 A | 1/2007 |
| JP | 2008515974 A | 5/2008 |
| RU | 2092483 C1 | 10/1997 |
| WO | WO 95/07284 A1 | 3/1995 |
| WO | WO 2004/033447 | 4/2004 |
| WO | WO 20061044293 A2 | 4/2006 |
| WO | WO 2008/136695 | 11/2008 |
| WO | WO-2008136695 A1 * | 11/2008 ........... C07D 405/04 |
| WO | 2009/064210 A2 | 5/2009 |
| WO | WO-2009113891 A1 * | 9/2009 ........... C07D 311/04 |
| WO | WO 2012/007548 A1 | 1/2012 |
| WO | WO 2012/175654 A1 | 12/2012 |
| WO | WO 2013/002660 A2 | 1/2013 |
| WO | 2015038022 A1 | 3/2015 |

OTHER PUBLICATIONS

Foreign communication from a related application—Second Office Action of Chinese Patent Application No. 201480050660.9 dated, Nov. 16, 2017, 30 pages including English Translation.

Al Neirabeyeh M. et al., Methoxy and hydroxyl derivatives of 3, 4-dihyrdro-3-(di-n-propylamino)-2H-1-benzopyrans : new synthesis and dopaminergic activity:, European Journal of Medicinal Chemistry, vol. 26, No. 5, 1991, pp. 497-504, Editions Scientifique Elsevier, Paris; FR.

Beliaev, A. et al., "Process Research for Multikilogram Production of Etamicastat: A Novel Dopamine β-Hydroxylase Inhibitor", Organic Process Research & Development, No. 16, 2012, pp. 704-709, American Chemical Society, Washington, U.S.

Boye, S. et al., "N, N-Disubstituted aminomethyl benzofuran derivatives: synthesis and preliminary binding evaluation", Bioorganic & Medicinal Chemistry, No. 7, 1999, pp. 335-341; Elsevier Science Ltd. GB.

Comoy, C. et al., "3-Amino-3, 4-dihydro-Sh-1-benzopyran Derivatives as 5-HT1A Receptor Ligandsand Potential Anxiolytic Agents. 2. Synthesis and QuantitativeStructure-Activity Relationship Studies of Spiro[pyrrolidine-andpiperidine-2,3' (2'H)-benzopyrans]", Journal of Medical Chemistry., vol. 39, No. 21, 199, pp. 4285-4298, American Chemical Society. Washington; US.

International Search Report and Written Opinion for PCT/PT2014/000061 prepared by European Patent Office (18 pages).

Search Report under Section 17(5) for GB 1320366.6, prepared by the Intellectual Property Office, dated Jul. 25, 2014.(5 pages).

Shin, C. et al., "Total Synthesis of Bistratamide G, a Metabolite of the PhilippinesAscidian Lissoclinum bistratum, from Dehydrotripeptides", Chemistry Letters, vol. 33, No. 6, 2004, pp. 664-665. Chemical Society of Japan, Tokyo; JP.

Vasse, J. L. et al., "New Efficient Conditions for the Reduction with NADH models", Synlett, Oct. 1998, pp. 1144-1146; Thieme International, Stuttgart; DE.

Xiao, G.-Q. et al., "3-Nitro-SH-chromenes as a New Class of Inhibitors against Thioredoxin Reductase and Proliferation of Cancer Cells", Archiv der Pharmazie, No. 345, 2012, pp. 767-770; VCH Verlagsgesellschaft MBH, Weinheim; DE.

Foreign communication from a related application—Examination Report of European Patent Application No. 14 772 233.4, dated Nov. 12, 2018, 3 pages.

Foreign communication from a related application—Office Action of Japanese Patent Application No. P2016-541935, dated Jul. 10, 2018, with English translation, 10 pages.

Foreign communication from a related application—Office Action and Search Report of Russian Patent Application No. 2016113965, dated Jun. 8, 2018, with English translation, 24 pages.

Crooks, Peter A., et al., "Synthesis of spiro[tetralin-2,2'-pyrrolidine] and spiro[indan-2,2'-pyrrolidine] derivatives as potential analgesics," Journal of Medicinal Chemistry, 1978, pp. 585-587, vol. 21, No. 6, American Chemical Society.

Sader-Bakaouni, Lina, et al., "Intramolecular Diels-Alder reaction of dinitro-olefin derivatives of furan for the preparation of a versatile tool: 3,7-dinitro-11-oxatricycloundec-9-ene," Tetrahedron, 1998, pp. 1773-1782, vol. 54, Elsevier Science Ltd.

Toogood, Helen S., "Structure-Based Insight into the Asymmetric Bioreduction of the C=C Double Bond of α,β Unsaturated Nitroalkenes by Pentaerythritol Tetranitrate Reductase," Adv Synth Catal., Nov. 17, 2008, pp. 2789-2803, vol. 350, No. 17, Wiley-VCH Verlag GmbH & Co. KGaA, Weinheim.

Database Registry (STN) RN 1314976-86-7, [online], Aug. 4, 2011, [Retrieved on Jun. 27, 2017].

Database Registry (STN) RN 1314962-26-9, [online], Aug. 4, 2011, [Retrieved on Jun. 27, 2017].

Foreign communication from a related application—Office Action of Japanese Patent Application No. P2016-541935, dated Jan. 22, 2019, with English translation, 5 pages.

* cited by examiner

PROCESSES FOR PREPARING MEDICAMENTS FOR THE TREATMENT OF CARDIOVASCULAR DISEASES AND INTERMEDIATES FOR USE THEREIN

The present invention relates to improved processes for preparing intermediates useful in the synthesis of peripherally-selective inhibitors of dopamine-β-hydroxylase. The present invention also relates to novel compounds for use in the processes.

(R)-5-(2-Aminoethyl)-1-(6,8-difluorochroman-3-yl)-1,3-dihydroimidazole-2-thione hydrochloride (the compound of formula 1, below) is a potent, non-toxic and peripherally selective inhibitor of DβH, which can be used for treatment of certain cardiovascular disorders. Compound 1 is disclosed in WO2004/033447, along with processes for its preparation.

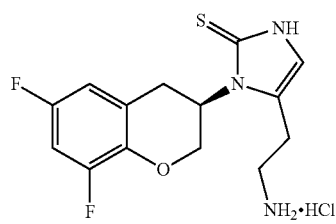

1

The process disclosed in WO2004/033447 involves the reaction of (R)-6,8-difluorochroman-3-ylamine hydrochloride (the structure of (R)-6,8-difluorochroman-3-ylamine is shown below as compound QA), [4-(tert-butyldimethylsilanyloxy)-3-oxobutyl]carbamic acid tert-butyl ester and potassium thiocyanate.

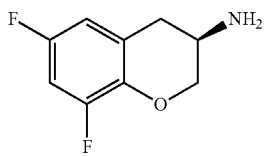

QA (R)-6,8-difluorochroman-3-ylamine (compound QA) is a key intermediate in the synthesis of compound 1. The stereochemistry at the carbon atom to which the amine is attached gives rise to the stereochemistry of compound 1, so it is advantageous that compound QA is present in as pure enantiomeric form as possible. In other words, the (R)-enantiomer of compound QA should be in predominance, with little or no (S) enantiomer present. Thus, the process for preparing compound QA will advantageously produce compound QA with as high enantiomeric excess (ee) as possible.

Advantageous processes for preparing, for example, the compound of formula QA have now been found. In one aspect, the processes involve a biotransformation step. In another aspect, the processes involve chemical transformation. The processes may also be employed in the preparation of similar precursors useful in the production of other peripherally-selective inhibitors of dopamine-β-hydroxylase.

WO2008/136695 discloses a compound of formula YA, its (R) or (S) enantiomer, a mixture of its (R) and (S) enantiomers, or pharmaceutically acceptable salts thereof.

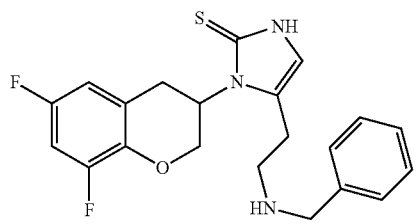

YA

The (R)-enantiomer of the compound of formula YA has been found to be a potent dopamine-β-hydroxylase inhibitor having high potency and significantly reduced brain access.

As disclosed in WO2008/136695, the compound of formula YA may be prepared by reacting the compound of formula 1 with benzaldehyde under reductive alkylation conditions. In particular, (R)-5-(2-aminoethyl)-1-(6,8-difluorochroman-3-yl)-1,3-dihydroimidazole-2-thione and benzaldehyde may be reacted in the presence of a solvent or mixture of solvents, and a reducing agent such as sodium cyanoborohydride or sodium triacetoxyborohydride.

SUMMARY OF THE INVENTION

According to one aspect of the present invention, there is provided the (R)- or (S)-enantiomer of a compound of formula N, or a mixture of the (R)- and (S)-enantiomers

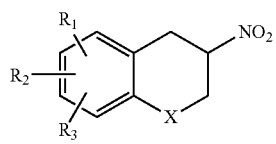

N wherein: X is $CH_2$, oxygen or sulphur; $R_1$, $R_2$ and $R_3$ are the same or different and signify hydrogens, halogens, alkyl, alkyloxy, hydroxy, nitro, alkylcarbonylamino, alkylamino or dialkylamino group, wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine.

X may be oxygen. Optionally, one of $R_1$, $R_2$ and $R_3$ is hydrogen, and the others are halo; suitably fluorine, chlorine, bromine or iodine. Preferably, the moieties at the 5- and 7-positions of the aromatic ring are both hydrogen and the groups at the 6- and 8-positions are both halo; suitably both fluorine, chlorine, bromine or iodine. Preferably, the halo groups are fluorine or bromine; most preferably fluorine (which is the compound of formula NA disclosed herein). Preferably, the compound is in the form of the (R)-enantiomer.

Preferably: X is O; the moiety at the 5- and 7-positions of the aromatic ring are hydrogen and the groups at the 6- and 8-positions are both fluorine, chlorine, bromine or iodine; and the compound is in the form of the (R)-enantiomer.

Preferably, the compound of formula N is in the form of the (R)-enantiomer and has the formula R-NA:

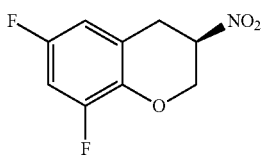

R-NA

The compound of formula N may be prepared from the corresponding compound of formula M:

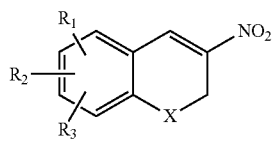

M wherein: X, $R_1$, $R_2$ and $R_3$ have the same meanings as given above.

X may be oxygen. Optionally, one of $R_1$, $R_2$ and $R_3$ is hydrogen, and the others are halo; suitably fluorine, chlorine, bromine or iodine. Preferably, the moieties at the 5- and 7-positions of the aromatic ring are both hydrogen and the groups at the 6- and 8-positions are both halo; suitably fluorine, chlorine, bromine or iodine. Preferably, the halo groups are fluorine or bromine; most preferably fluorine (which is the compound of formula MA disclosed herein).

Preferably: X is O; and the moiety at the 5- and 7-positions of the aromatic ring are hydrogen and the groups at the 6- and 8-positions are both fluorine, bromine or iodine; most preferably the groups at the 6- and 8-positions are both fluorine (this is the compound MA disclosed herein).

A preferred compound of formula M for use in the above process is the compound of formula MA, which forms another aspect of the present invention:

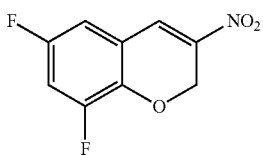

MA

Advantageously, compounds M and N are versatile products that may be used as starting materials or intermediates in a variety of processes.

According to one aspect of the present invention, there is provided the use of compound M as described above in a method of preparing a compound of formula Q, the individual (R)- or (S)-enantiomer of compound Q, or a mixture of the (R)- and (S)-enantiomer of compound Q; or a salt thereof.

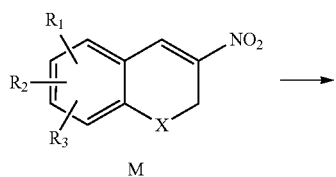

M

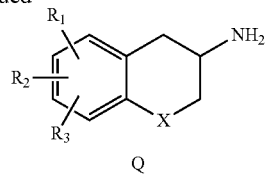

Q wherein: X, $R_1$, $R_2$ and $R_3$ are as defined above. X may be oxygen. Optionally, one of $R_1$, $R_2$ and $R_3$ is hydrogen, and the others are halo; suitably fluorine, chlorine, bromine or iodine. Preferably, the moieties at the 5- and 7-positions of the aromatic ring are both hydrogen and the groups at the 6- and 8-positions are both halo; suitably both fluorine, chlorine, bromine or iodine. Preferably, the halo groups are fluorine or bromine; most preferably fluorine.

Preferably, compound M is used to prepare the (R)-enantiomer of the compound Q. Preferably, compound MA is used to prepare compound QA or a salt thereof:

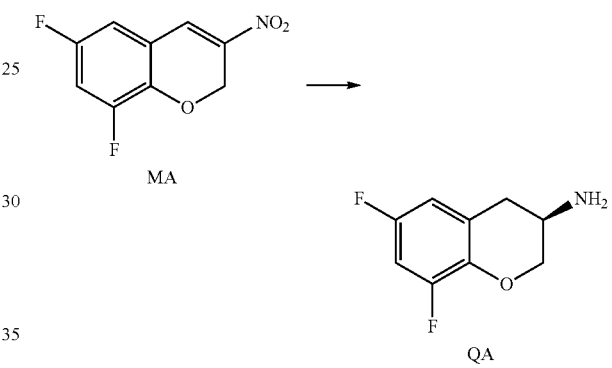

The compound of formula Q may be used to prepare the compounds of formula 1 and YA using any process disclosed herein or any process known in the prior art, for example using a process disclosed in WO2004/033447 or WO2008/136695.

Suitable salts of compound Q include the L-tartrate, hydrochloride, mesylate, tosylate, trifluotoacetate, citrate, glycolate, oxalate and acetate salts. The preferred salt is the L-tartrate salt. Suitably, compound QA is prepared either in free base form or as the L-tartrate salt thereof. Preferably, compound QA is prepared as the L-tartrate salt thereof.

According to an aspect of the present invention, there is provided a process for preparing compound MB, the process comprising reacting a compound of formula R with 2-nitroethanol or nitroethylene to obtain the compound MB.

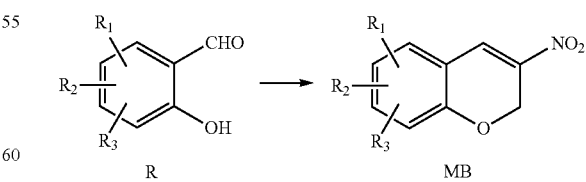

Compound MB is the compound of formula M, wherein X is O. $R_1$, $R_2$ and $R_3$ are as defined above. Optionally, one of $R_1$, $R_2$ and $R_3$ is hydrogen, and the others are halo; suitably fluorine, chlorine, bromine or iodine. Preferably, the moieties at the 5- and 7-positions of the aromatic ring are both hydrogen and the groups at the 6- and 8-positions are both halo; suitably both fluorine, chlorine, bromine or iodine. Preferably, the halo groups are fluorine or bromine; most preferably fluorine.

The process is suitably carried out in the presence of a solvent, a base and phthalic anhydride. The base is suitably dibutylamine and the solvent is suitably toluene.

The compound of formula R may be prepared by any known method. Such methods are disclosed in WO2009/064210 and Beliaev et al, Org. Process Res. Dev., 2012, 16 (4), pp 704-709. For example, compound R may be prepared by reacting a compound of formula IV with a formylating agent such as hexamethylenetetramine and an acid such as acetic acid.

IV

Preferably, compound RA (3,5-difluoro-2-hydroxybenzaldehyde) is prepared by reacting 2,4-difluorophenol with hexamethylenetetramine and trifluoroacetic acid.

The compounds of formula M and N as described herein and as prepared by the processes described herein may be used in any one of the following processes, all of which form aspects of the present invention.

According to an aspect of the present invention, there is provided a process for preparing a pro-chiral ketone chromanone compound of formula W, the process comprising the conversion of a compound of formula M to the compound of formula W

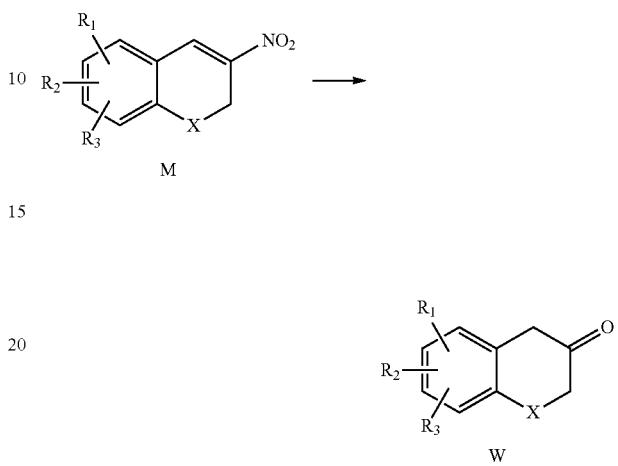

wherein: X, $R_1$, $R_2$ and $R_3$ are as defined above. Suitably, the conversion comprises reaction of compound M with iron and acetic acid. Preferably, the compound of formula WA is prepared by reacting a compound of formula MA, suitably in the presence of iron and acetic acid.

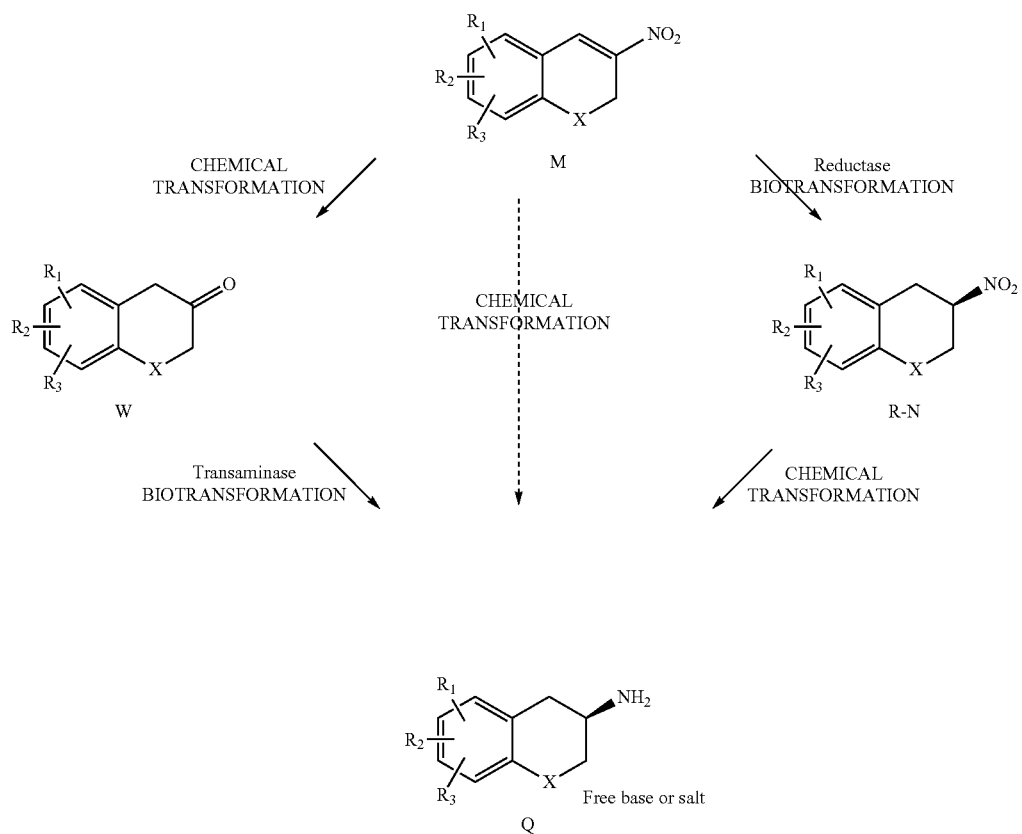

wherein: X, $R_1$, $R_2$ and $R_3$ are as defined above.

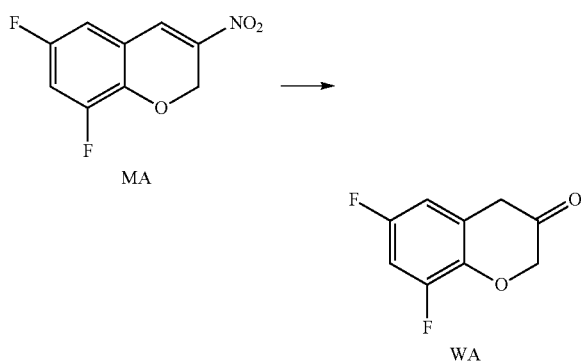

MA → WA

The present invention also provides the use of a biotransformation process to obtain the (R)- or the (S)-enantiomer of the compound of formula Q, or a salt thereof. Suitable salts are described above.

Thus, according to one aspect of the present invention, there is provided a process for preparing the (R)-enantiomer (R-Q) or the (S)-enantiomer (S-Q) of a compound of formula Q, the process comprising the biotransformation of a compound of formula W via transamination using an transaminase enzyme and an amine group donor.

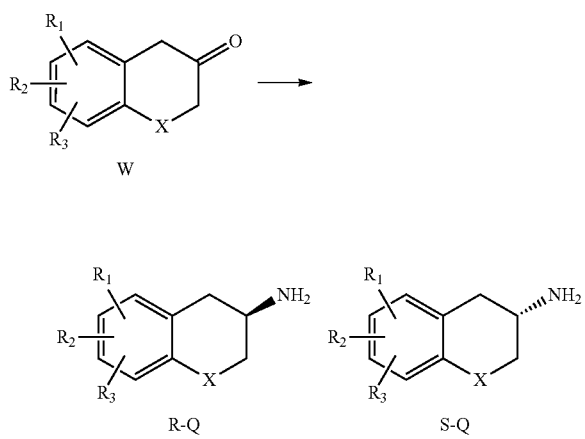

The enzyme is a transaminase, which may also be referred to as an aminotransferase. The enzyme is suitably a polypeptide having transaminase activity. Suitably, the enzyme is an engineered enzyme.

The amine group donor may be selected from isopropylamine, alanine, 3-aminobutyric acid and methylbenzylamine. Preferably, the amine group donor is isopropylamine. The amine group donor is suitably provided as a salt thereof. Preferably, the amino donor is provided as isopropylamine HCl.

Preferably, the transamination is enantioselective, and one enantiomer is provided in enantiomeric excess relative to the other enantiomer. Enantiomeric excess is calculated as [major enantiomer-minor enantiomer]/[major enantiomer+minor enantiomer], as a percentage. Preferably, one enantiomer is produced in at least 50% enantiomeric excess. More preferably the enantiomer is produced in at least 70% enantiomeric excess. Still more preferably the enantiomer is produced in at least 80% enantiomeric excess. Most preferably the enantiomer is produced in at least 90% enantiomeric excess. Preferred transaminases are those that result in an enantiomeric excess of at least 50%. More preferred transaminases are those that result in an enantiomeric excess of the R-enantiomer of compound Q of at least 50%.

Preferably, the reaction is carried out under conditions suitable for producing the desired enantiomer (i.e. the major enantiomer) in enantiomeric excess compared to the minor enantiomer.

The enzyme may be selected from any one of the enzymes disclosed in U.S. Pat. No. 8,293,507.

The following enzymes may be used as the transaminase in the above process:

Supplier: Johnson Matthey
Kit Name: X-zyme
Supplier code: Not available
Kit content: 36 transaminases and co factor PLP
Supplier: Prozomix
Kit name: Transaminase Panel (kit of 200 enzymes)
Supplier code: PRO-TRANSP
Kit content: 200 enzymes
Supplier: Codexis
Kit Name: Codex® ATA Screening Kit
Supplier code: ATASK-200250
Kit content: 24 transaminases and co-factor PLP
Code of enzymes: ATA-007, ATA-013, ATA-025, ATA-113, ATA-117, ATA-200, ATA-217, ATA-234, ATA-237, ATA-238, ATA-251, ATA-254, ATA-256, ATA-260, ATA-301, ATA-303, ATA-412, ATA-415, ATA-P1-B04, ATA-P1-F03, ATA-P1-G05, ATA-P2-A01, ATA-P2-A07 and ATA-P2-B01

ATA-025 and ATA-P2-A07 produce the (S)-enantiomer of compound QA in enantiomeric excess. ATA-251 produces the (R)-enantiomer of compound QA in enantiomeric excess.

The transamination is suitably carried out in the presence of a cofactor for the enzyme. The cofactor is preferably pyridoxal-5'-phosphate (PLP).

The transamination reaction may be carried out in a solvent selected from dimethylsulfoxide (DMSO), acetonitrile, heptane, tetrahydrofuran (THF), ethyl acetate, 2-propanol and methyl t-butyl ether (MTBE).

It was found that the use of DMSO was particularly advantageous when the transaminase was ATA-251 and the substrate was the compound of formula WA. The transamination reaction resulted in the R-enantiomer of the compound of formula QA, and the enantiomeric excess of the R-enantiomer was 90%.

The transamination reaction may be carried out in a buffer solution. The buffer solution may be an aqueous solution of triethanolamine HCl. The concentration of the triethanolamine HCl in the buffer solution may be around 200 mM. The pH of the solution may be adjusted with HCl to range from around 7 to around 8, preferably around 7.5.

The pH of the transaminase reaction is typically maintained above 7, preferably between around 7 and around 9, more preferably between around 7 and around 8.5.

The temperature of the transamination reaction may range from about 25° C. to about 50° C. Preferably, the temperature ranges from about 25° C. to about 40° C. Typically, the temperature is around 30° C.

The preferred transamination reaction may be represented as:

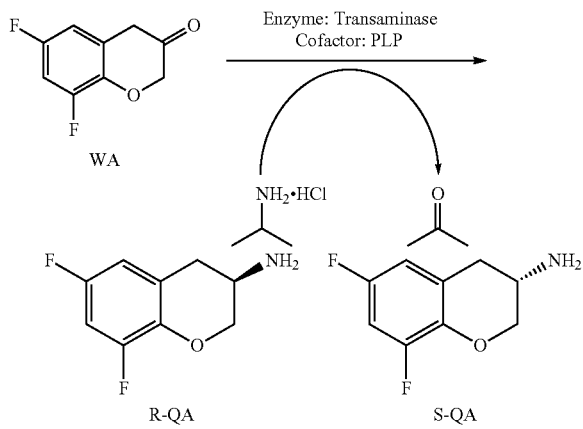

The preferred reagents/conditions for the above transamination of WA are:

Enzyme: ATA-251
Cofactor: PLP
Amino donor: isopropylamine HCl
Buffer: aqueous triethanolamine HCl
Solvent: DMSO Typically, the transamination process typically comprises the following steps:
(a) preparation of buffer solution (Solution 1):
(b) preparation of amine group donor solution (Solution 2):
(c) preparation of cofactor/buffer solution (Solution 3)
(d) addition of Solution 3 to enzyme (Solution 4)
(e) addition of Solution 2 to Solution 4 (Solution 5)
(f) addition of substrate to Solution 5 (Solution 6)
(g) addition of Solution 1 to Solution 6 (Solution 7)
(h) addition of solvent to Solution 7
(i) upon reaction completion, addition of organic solvent such as ethyl acetate
(j) isolation of product.

The compound of formula W may be prepared using a process as disclosed herein from the nitro chromene compound M.

The compound of formula WA may also be prepared using a process comprising bromination of 2,4-difluorophenol to give bromophenol, alkylation of bromophenol with 4-chloro-3-oxo butanoate to give ketone followed by cyclization and decarboxylation to produce compound WA.

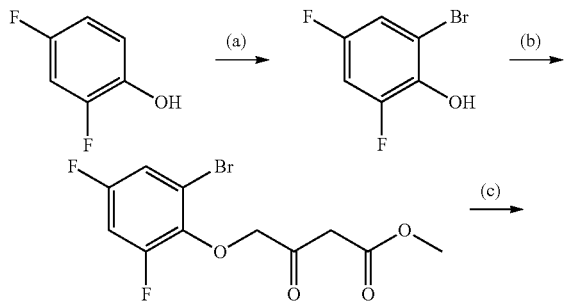

Suitable reagents and conditions are:
a) $Br_2$, water, 0-5° C., 2 hours;
b) 4-chloro-3-oxobutanoate, KOH, DMSO, room temperature,
c) CuI, DMEDA, base, heating in organic solvent followed by 20% $H_2SO_4$ at reflux.

The compound of formula W may also be prepared from the corresponding ene carbamate of formula S, where the process comprises the reaction of the compound of formula S in the presence of HCl and methanol. Other acids and solvents may be used: for instance, trifluoroacetic acid or sulfuric acid may be used instead.

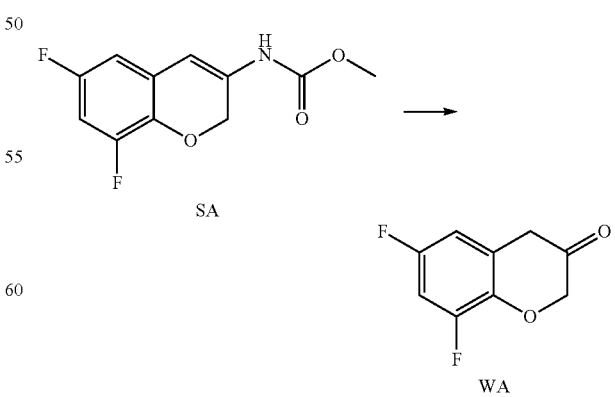

wherein: X, $R_1$, $R_2$ and $R_3$ are as defined above, and $R_4$ is alkyl or aryl, wherein: the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyloxy, halogen or nitro group; and the term halogen means fluorine, chlorine, bromine or iodine. Suitably, $R_4$ is $C_1$ to $C_4$ alkyl or benzyl. Optionally, $R_4$ is methyl, ethyl or t-butyl. Preferably, $R_4$ is methyl. Most preferably, the conversion comprises:

According to an aspect of the present invention, there is provided a process for preparing a compound of formula Q, the process comprising converting a compound of formula M to the compound of formula Q. Thus, the invention provides a process for preparing a nitro chromane compound of formula N, the process comprising the reaction of a nitro chromene compound of formula M with a suitable reducing agent.

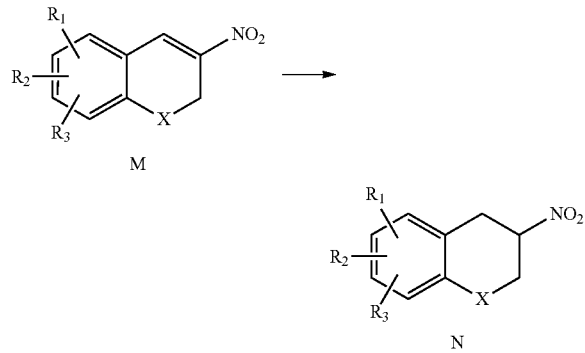

Preferably, the conversion comprises obtaining a compound of formula NA from a compound of formula MA. Preferably, the reducing agent is sodium borohydride. The reaction may be carried out in a solvent, which is suitably a mixture of chloroform and isopropanol.

The compound of formula N may then be resolved using a suitable technique to prepare the (R)-enantiomer (R-N) or the (S)-enantiomer (S-N) of the compound of formula N.

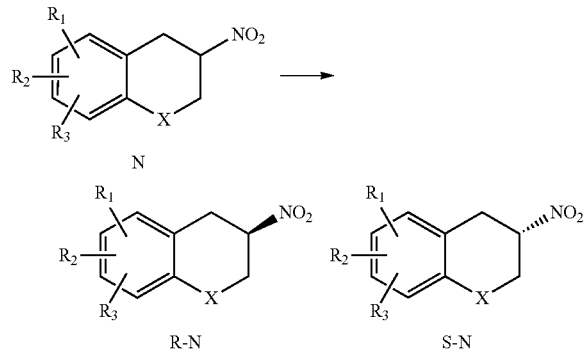

The resolved enantiomer of the compound of formula N may be converted to the corresponding enantiomer of the compound of formula Q, or a salt thereof, by suitable hydrogenation techniques. Preferably, the (R)-enantiomer of compound N is prepared, and that is then converted to the (R)-enantiomer of compound Q. The compound of formula R-Q may be prepared in salt form, for example as the HCl salt thereof.

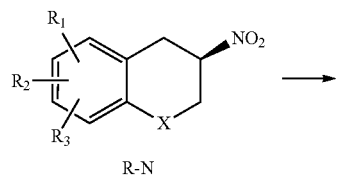

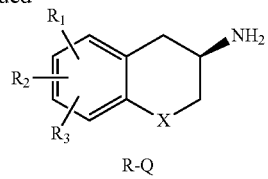

Preferably, the hydrogenation involves obtaining a compound of formula R-QA from a compound of formula R-NA. The hydrogenation may involve the use of hydrazine hydrate and Raney-Nickel. Other suitable hydrogenation conditions include: use of Raney-Nickel under a hydrogen atmosphere; or use of a catalyst such as Palladium (typically supported on charcoal) under a hydrogen atmosphere, or in the presence of a hydrogen donor compound such as formic acid, ammonium formate, or hydrazine hydrate.

According to an aspect of the present invention, there is provided a process for preparing the (R)-enantiomer (R-Q) or the (S)-enantiomer (S-Q) of the compound of formula Q or a salt thereof, the process comprising a biotransformation of nitro chromene compound M to the (R)-enantiomer (R-N) or the (S)-enantiomer (S-N) of a compound of formula N in the presence of a reductase enzyme, and converting the (R)-enantiomer (R-N) or the S-enantiomer (S-N) of the compound of formula N to the corresponding R-enantiomer (R-Q) or the (S)-enantiomer (S-Q) of the compound of formula Q or salt thereof.

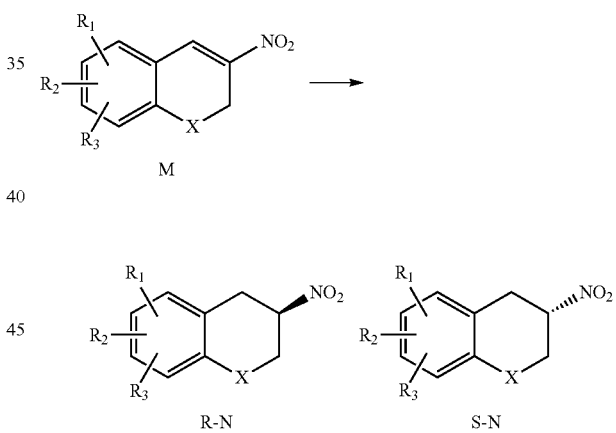

The R- or S-enantiomer of the compound of formula N may be converted to the corresponding (R)- or (S)-enantiomer of the compound of formula Q, or a salt thereof, by suitable hydrogenation techniques. The (R)- or (S)-enantiomer of the compound of formula R may be converted to the corresponding (R)- or (S)-enantiomer of the compound of formula Q in free base form which is subsequently converted to a salt thereof. Preferably, the compound of formula M is converted to the (R)-enantiomer of the compound of formula N, which is then converted to the (R)-enantiomer of the compound of formula Q, or a salt thereof; preferably, the salt is the HCl salt. More preferably, the compound of formula MA is converted to the (R)-enantiomer of the compound of formula NA, which is then converted to the (R)-enantiomer of the compound of formula QA, or a salt thereof; preferably, the salt is the HCl salt.

Suitably, the process comprises the following steps:

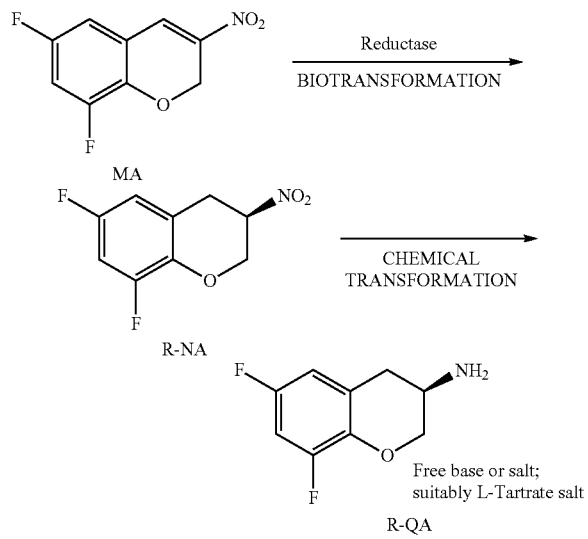

The hydrogenation from the nitro chromane to the amine chromane may involve the use of hydrazine hydrate and Raney-Nickel. Other suitable hydrogenation conditions include: use of Raney-Nickel under a hydrogen atmosphere; or use of a catalyst such as Palladium (typically supported on charcoal) under a hydrogen atmosphere, or in the presence of a hydrogen donor compound such as formic acid, ammonium formate, or hydrazine hydrate.

The (R)- or S-enantiomer of the compound of formula Q, or a salt thereof, may be converted to the respective (R)- or S-enantiomer of a compound of formula E or a salt thereof

E wherein $R_1$, $R_2$, and $R_3$ have the same meanings as given above; $R_{12}$ signifies hydrogen, alkyl or alkylaryl group; and n is 1, 2 or 3. Preferably E is (R)-5-(2-aminoethyl)-1-(6,8-difluorochroman-3-yl)-1,3-dihydroimidazole-2-thione or (R)-5-(2-aminoethyl)-1-(6,8-difluorochroman-3-yl)-1,3-dihydroimidazole-2-thione hydrochloride.

In an embodiment, the (R)- or S-enantiomer of the compound of formula Q is reacted with a compound of formula D2

D2 to produce the respective (R)- or S-enantiomer of a compound of formula E or salt thereof

E where $R_1$, $R_2$ and $R_3$ have the same meanings as given above n signifies 1, 2 or 3; $R_{12}$ signifies hydrogen, alkyl or alkylaryl group, $R_{11}$ signifies a hydroxyl protecting group and $R_{13}$ signifies an amino protecting group, or $R_{11}$ is defined as above but $R_{12}$ and $R_{13}$ taken together represent a phthalimido group; with a water soluble thiocyanate salt in the presence of an organic acid in a substantially inert solvent, followed by subsequent deprotection of the intermediate products F to I:

F

G

H

I

Preferably, the water soluble thiocyanate salt is an alkali metal thiocyanate salt or a tetraalkylammonium thiocyanate salt. Preferably the solvent is an organic solvent.

In an embodiment, n is 2 or 3. In a further embodiment, at least one of $R_1$, $R_2$ and $R_3$ is fluorine. Two of $R_1$, $R_2$ and $R_3$ may be fluorine. Optionally, the compound of formula E is:
(S)-5-(2-aminoethyl)-1-(1,2,3,4-tetrahydronaphthalen-2-yl)-1,3-dihydroimidazole-2-thione;
(S)-5-(2-aminoethyl)-1-(5,7-difluoro-1,2,3,4-tetrahydronaphthalen-2-yl)-1,3-dihydroimidazole-2-thione;

(R)-5-(2-aminoethyl)-1-chroman-3-yl-1,3-dihydroimidazole-2-thione;
(R)-5-(2-aminoethyl)-1-(6-hydroxychroman-3-yl)-1,3-dihydroimidazole-2-thione;
(R)-5-(2-aminoethyl)-1-(8-hydroxychroman-3-yl)-1,3-dihydroimidazole-2-thione;
(R)-5-(2-aminoethyl)-1-(6-methoxychroman-3-yl)-1,3-dihydroimidazole-2-thione;
(R)-5-(2-aminoethyl)-1-(8-methoxychroman-3-yl)-1,3-dihydroimidazole-2-thione;
(R)-5-(2-aminoethyl)-1-(6-fluorochroman-3-yl)-1,3-dihydroimidazole-2-thione;
(R)-5-(2-aminoethyl)-1-(8-fluorochroman-3-yl)-1,3-dihydroimidazole-2-thione;
(R)-5-(2-aminoethyl)-1-(6,7-difluorochroman-3-yl)-1,3-dihydroimidazole-2-thione;
(R)-5-(2-aminoethyl)-1-(6,8-difluorochroman-3-yl)-1,3-dihydroimidazole-2-thione;
(S)-5-(2-aminoethyl)-1-(6,8-difluorochroman-3-yl)-1,3-dihydroimidazole-2-thione;
(R)-5-(2-aminoethyl)-1-(6,7,8-trifluorochroman-3-yl)-1,3-dihydroimidazole-2-thione;
(R)-5-(2-aminoethyl)-1-(6-chloro-8-methoxychroman-3-yl)-1,3-dihydroimidazole-2-thione;
(R)-5-(2-aminoethyl)-1-(6-methoxy-8-chlorochroman-3-yl)-1,3-dihydroimidazole-2-thione;
(R)-5-(2-aminoethyl)-1-(6-nitrochroman-3-yl)-1,3-dihydroimidazole-2-thione;
(R)-5-(2-aminoethyl)-1-(8-nitrochroman-3-yl)-1,3-dihydroimidazole-2-thione;
(R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione;
(R)-5-aminomethyl-1-(6-hydroxychroman-3-yl)-1,3-dihydroimidazole-2-thione;
(R)-5-(2-aminoethyl)-1-(6-hydroxy-7-benzylchroman-3-yl)-1,3-dihydroimidazole-2-thione;
(R)-5-aminomethyl-1-(6,8-difluorochroman-3-yl)-1,3-dihydroimidazole-2-thione;
(R)-5-(3-aminopropyl)-1-(6,8-difluorochroman-3-yl)-1,3-dihydroimidazole-2-thione;
(S)-5-(3-aminopropyl)-1-(5,7-difluoro-1,2,3,4-tetrahydronaphthalen-2-yl)-1,3-dihydroimidazole-2-thione;
(R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione;
(R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione.

It will be appreciated that the $R_1$, $R_2$ and $R_3$ groups on the compounds of M, N and Q may be selected such that they correspond to the $R_1$, $R_2$ and $R_3$ groups on the compound E of interest. For example, if the compound E of interest is (R)-5-(2-aminoethyl)-1-(6-hydroxychroman-3-yl)-1,3-dihydroimidazole-2-thione, the compound N will be (R)-6-hydroxy-3-nitro chromane, the compound M will be 6-hydroxy-3-nitro chromene and so on. The compounds M, N and Q corresponding to the compounds of formula E listed above define further aspects of the present invention.

The compound of formula E may also be a salt of:
(S)-5-(2-aminoethyl)-1-(1,2,3,4-tetrahydronaphthalen-2-yl)-1,3-dihydroimidazole-2-thione;
(S)-5-(2-aminoethyl)-1-(5,7-difluoro-1,2,3,4-tetrahydronaphthalen-2-yl)-1,3-dihydroimidazole-2-thione;
(R)-5-(2-aminoethyl)-1-chroman-3-yl-1,3-dihydroimidazole-2-thione;
(R)-5-(2-aminoethyl)-1-(6-hydroxychroman-3-yl)-1,3-dihydroimidazole-2-thione;
(R)-5-(2-aminoethyl)-1-(8-hydroxychroman-3-yl)-1,3-dihydroimidazole-2-thione;
(R)-5-(2-aminoethyl)-1-(6-methoxychroman-3-yl)-1,3-dihydroimidazole-2-thione;
(R)-5-(2-aminoethyl)-1-(8-methoxychroman-3-yl)-1,3-dihydroimidazole-2-thione;
(R)-5-(2-aminoethyl)-1-(6-fluorochroman-3-yl)-1,3-dihydroimidazole-2-thione;
(R)-5-(2-aminoethyl)-1-(8-fluorochroman-3-yl)-1,3-dihydroimidazole-2-thione;
(R)-5-(2-aminoethyl)-1-(6,7-difluorochroman-3-yl)-1,3-dihydroimidazole-2-thione;
(R)-5-(2-aminoethyl)-1-(6,8-difluorochroman-3-yl)-1,3-dihydroimidazole-2-thione;
(S)-5-(2-aminoethyl)-1-(6,8-difluorochroman-3-yl)-1,3-dihydroimidazole-2-thione;
(R)-5-(2-aminoethyl)-1-(6,7,8-trifluorochroman-3-yl)-1,3-dihydroimidazole-2-thione;
(R)-5-(2-aminoethyl)-1-(6-chloro-8-methoxychroman-3-yl)-1,3-dihydroimidazole-2-thione;
(R)-5-(2-aminoethyl)-1-(6-methoxy-8-chlorochroman-3-yl)-1,3-dihydroimidazole-2-thione;
(R)-5-(2-aminoethyl)-1-(6-nitrochroman-3-yl)-1,3-dihydroimidazole-2-thione;
(R)-5-(2-aminoethyl)-1-(8-nitrochroman-3-yl)-1,3-dihydroimidazole-2-thione;
(R)-5-(2-aminoethyl)-1-[6-(acetylamino)chroman-3-yl]-1,3-dihydroimidazole-2-thione; (R)-5-aminomethyl-1-chroman-3-yl-1,3-dihydroimidazole-2-thione;
(R)-5-aminomethyl-1-(6-hydroxychroman-3-yl)-1,3-dihydroimidazole-2-thione;
(R)-5-(2-aminoethyl)-1-(6-hydroxy-7-benzylchroman-3-yl)-1,3-dihydroimidazole-2-thione;
(R)-5-aminomethyl-1-(6,8-difluorochroman-3-yl)-1,3-dihydroimidazole-2-thione;
(R)-5-(3-aminopropyl)-1-(6,8-difluorochroman-3-yl)-1,3-dihydroimidazole-2-thione;
(S)-5-(3-aminopropyl)-1-(5,7-difluoro-1,2,3,4-tetrahydronaphthalen-2-yl)-1,3-dihydroimidazole-2-thione;
(R,S)-5-(2-aminoethyl)-1-(6-hydroxythiochroman-3-yl)-1,3-dihydroimidazole-2-thione; (R,S)-5-(2-aminoethyl)-1-(6-methoxythiochroman-3-yl)-1,3-dihydroimidazole-2-thione; (R)-5-(2-benzylaminoethyl)-1-(6-methoxychroman-3-yl)-1,3-dihydroimidazole-2-thione;
(R)-5-(2-benzylaminoethyl)-1-(6-hydroxychroman-3-yl)-1,3-dihydroimidazole-2-thione; (R)-1-(6-hydroxychroman-3-yl)-5-(2-methylaminoethyl)-1,3-dihydroimidazole-2-thione; (R)-1-(6,8-difluorochroman-3-yl)-5-(2-methylaminoethyl)-1,3-dihydroimidazole-2-thione or (R)-1-chroman-3-yl-5-(2-methylaminoethyl)-1,3-dihydroimidazole-2-thione. Preferably the salt is the hydrochloride salt.

The compound of formula E or salt thereof may be used to prepare the compound of formula Y. Thus, the compound of formula E or salt thereof prepared by a process disclosed herein may be used in a process for the preparation of the individual (R)- and (S)-enantiomers or mixtures of enantiomers and pharmaceutically acceptable salts of a compound of formula Y, which process comprises reacting the individual (R)- or (S)-enantiomers or mixtures of enantiomers of a compound of Formula III with a compound of formula IX under reductive alkylation conditions

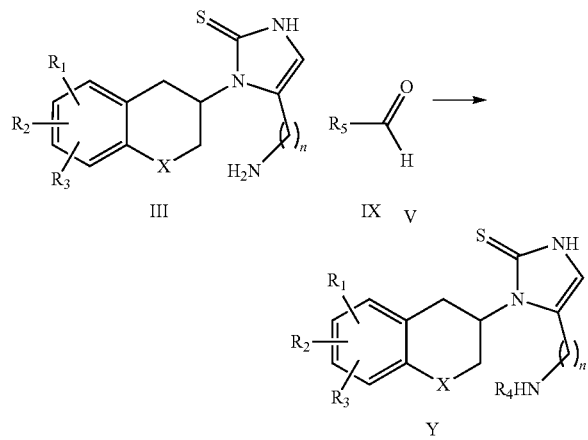

where $R_1$, $R_2$ and $R_3$ are the same or different and signify hydrogen, halogen, alkyl, nitro, amino, alkylcarbonylamino, alkylamino or dialkylamino group; $R_4$ signifies -alkyl-aryl or -alkyl-heteroaryl; $R_5$ signifies aryl or heteroaryl, X signifies $CH_2$, oxygen atom or sulphur atom; n is 2 or 3; wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyl, alkyloxy, halogen or nitro group; the term halogen means fluorine, chlorine, bromine or iodine; the term heteroaryl means heteroaromatic group.

The compound of formula R-YA or salt thereof may also be prepared by reacting a compound of formula R-QA prepared by any process disclosed herein with a compound of formula C, to obtain a compound of formula V, converting the compound of formula V to the compound of formula R-YA, and optionally converting the compound of formula R-YA to a salt thereof.

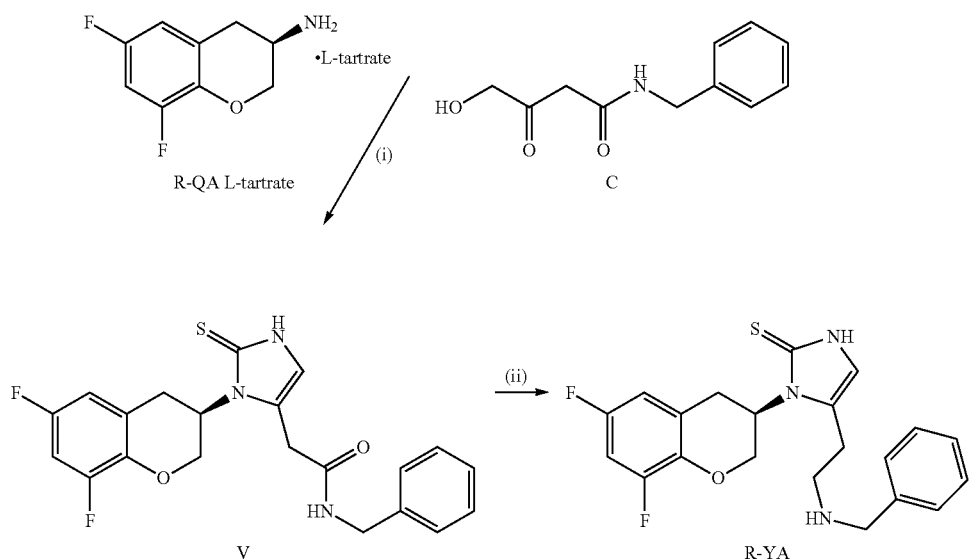

The reaction of compounds C and R-QA may be carried out in the presence of an alkali metal thiocyanate, preferably potassium thiocyanate (KSCN), and a suitable acid, preferably acetic acid.

The reduction of compound V to the compound R-YA may be carried out using a reducing agent comprising a $NaBH_4$—$BF_3$. complex such as $NaBH_4$—$BF_3$. Et2O, $NaBH_4$—$BF_3$.THF, preferably complex may be $NaBH_4$—$BF_3$.THF.

The preferred reagents for the process are:
(i) KSCN, AcOH/IPA
(ii) $NaBH_4$, $BF_3$.THF, THF then IPA The compound of formula R-YA or salt thereof may also be prepared by reacting a compound of formula R-QA prepared by any process disclosed herein with a compound of formula VI to obtain a compound of formula VII, and the compound of formula VII is deprotected to obtain the compound of formula R-YA. Optionally, the compound of formula R-YA is converted to a salt thereof.

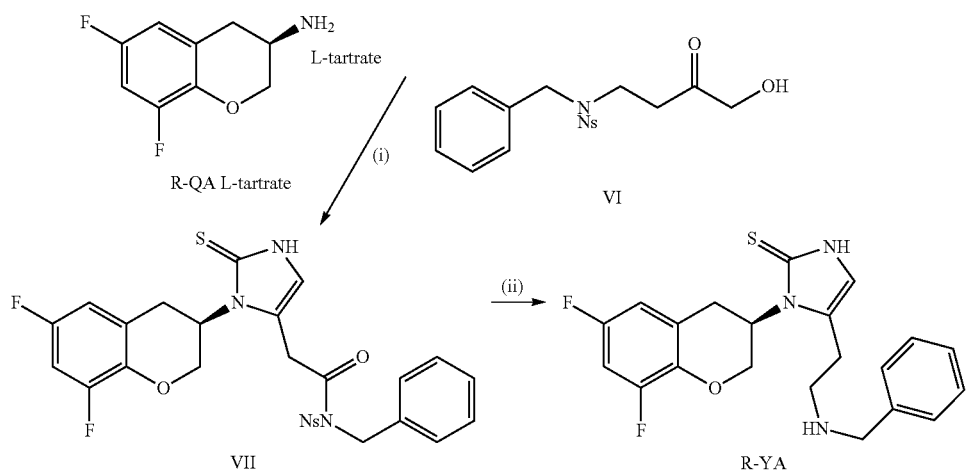

wherein Ns signifies o-nitrophenylsulphonyl.

Preferably, the deprotection step comprises treating a compound of formula VII with thioglycolic acid or cysteine in a suitable solvent, in the presence of a base, preferably LiOH or KOH.

Optionally, the compound R-YA is isolated from the deprotection step and purified. Preferably, purification is performed: via a two-step procedure comprising (i) formation of an HCl salt of a compound of formula RY and (ii) crystallisation of the HCl salt so formed from a suitable solvent, preferably toluene or isopropanol; or via a re-slurry in 2-butanone.

Preferably, the reaction of compounds VI and R-QA is carried out in the presence of an alkali metal thiocyanate, preferably potassium thiocyanate (KSCN), and a suitable acid, preferably acetic acid.

The compounds of formula C and VI may be prepared by a process as disclosed in WO2013/002660.

There is also disclosed herein the following advantageous routes for preparing a compound of formula YA, the (R)- or (S)-enantiomer thereof or a mixture of the (R)- and (S)-enantiomer, or a salt thereof. More specifically, there is provided novel advantageous routes for preparing compounds of formula R-YA or a pharmaceutically acceptable salt thereof.

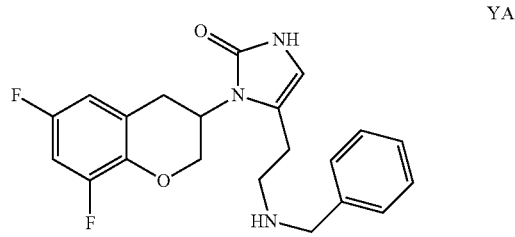 [SMILES: O=c1[nH]cc(CCNCc2ccccc2)n1C1COc2c(F)cc(F)cc2C1]

Preferably, the processes are to prepare the (R)-enantiomer of the compound of formula YA (R-YA) or a salt thereof. More preferably, the product is either the free base form of the compound of formula YA or the HCl salt of the (R)-enantiomer of compound YA.

In one aspect, the process comprises the following steps:

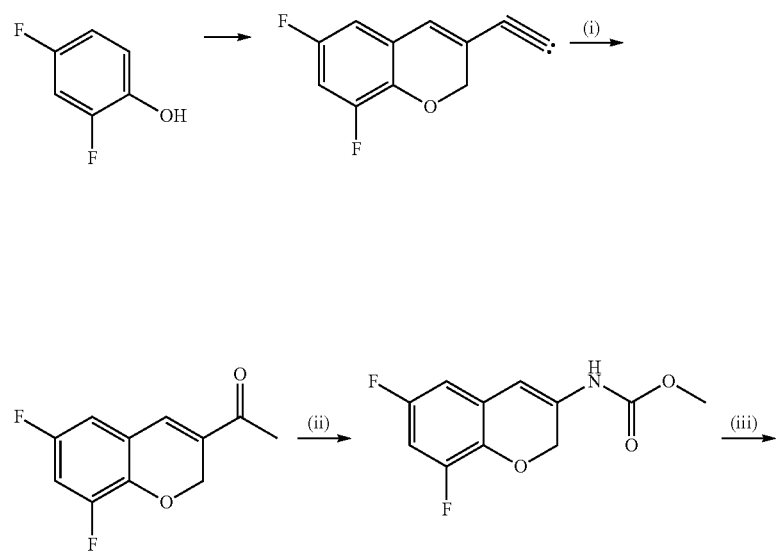

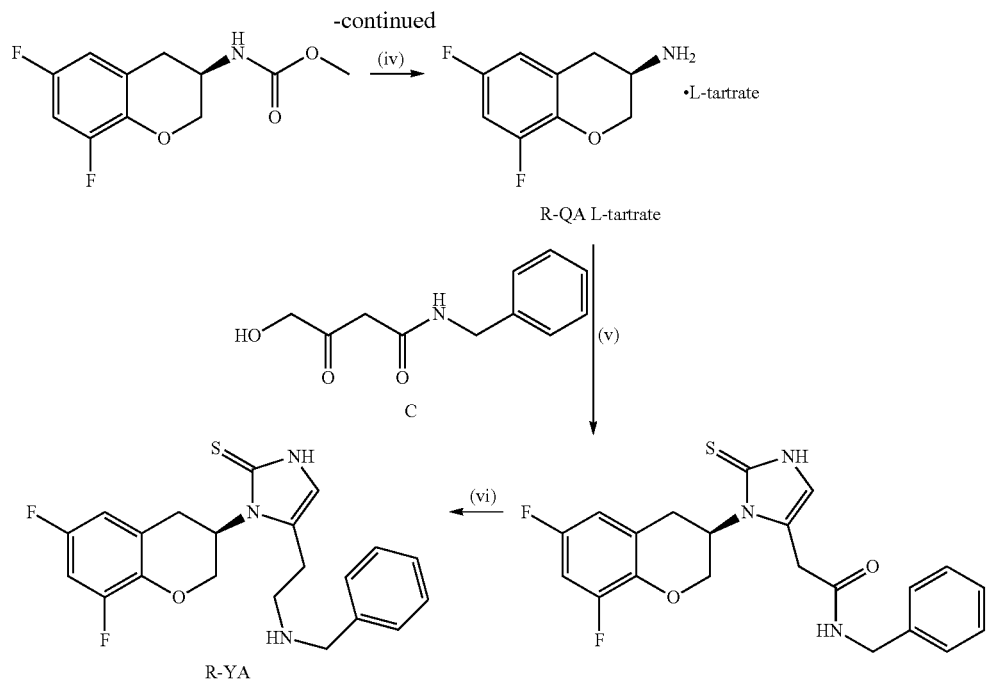

The route from 2,4-difluorophenol may be as described in WO2009/064210.

Preferably, the reagents and conditions are:
(i) H₂SO₄, acetic acid
(ii) NaOCl, MeOH/water
(iii) Ru-based catalyst, H₂, 30 bars, MeOH
(iv) aqueous KOH, MeOH, L-tartaric acid
(v) KSCN, AcOH/IPA
(vi) NaBH₄, BF₃.THF complex, THF then IPA In step (iii), the Ru-based catalyst may comprise a chiral bisphosphine ligand. The chiral bisphosphine ligand may be (R)-TolBINAP, (S)-TolBINAP, (R)-BINAP or (S)-BINAP. Alternatively, the ligand may be a chiral ligand having the formula below, wherein p is from 1 to 6, and Ar means aryl group.

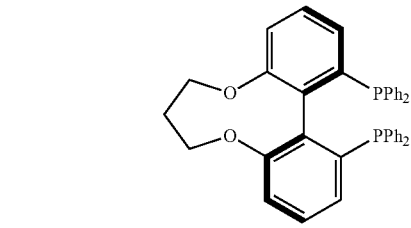

Such ligands and processes for their production are described in EP1214328A. Such ligands are from a series of ligands known under the name "TunePhos". The preferred TunePhos ligand is (R)-C3-TunePhos ligand which has the formula:

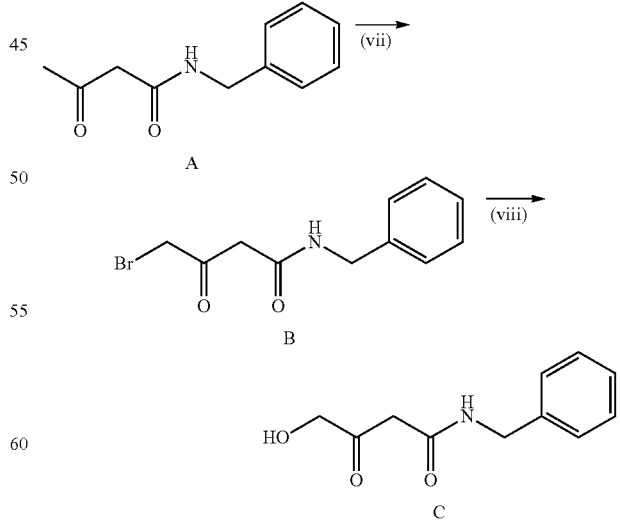

The compound of formula C is prepared according to the following process:

Preferably, the reagents and conditions are:
(vii) Br₂, DCM
(viii) KO₂CH, MeOH

In one aspect, the process comprises the following steps:
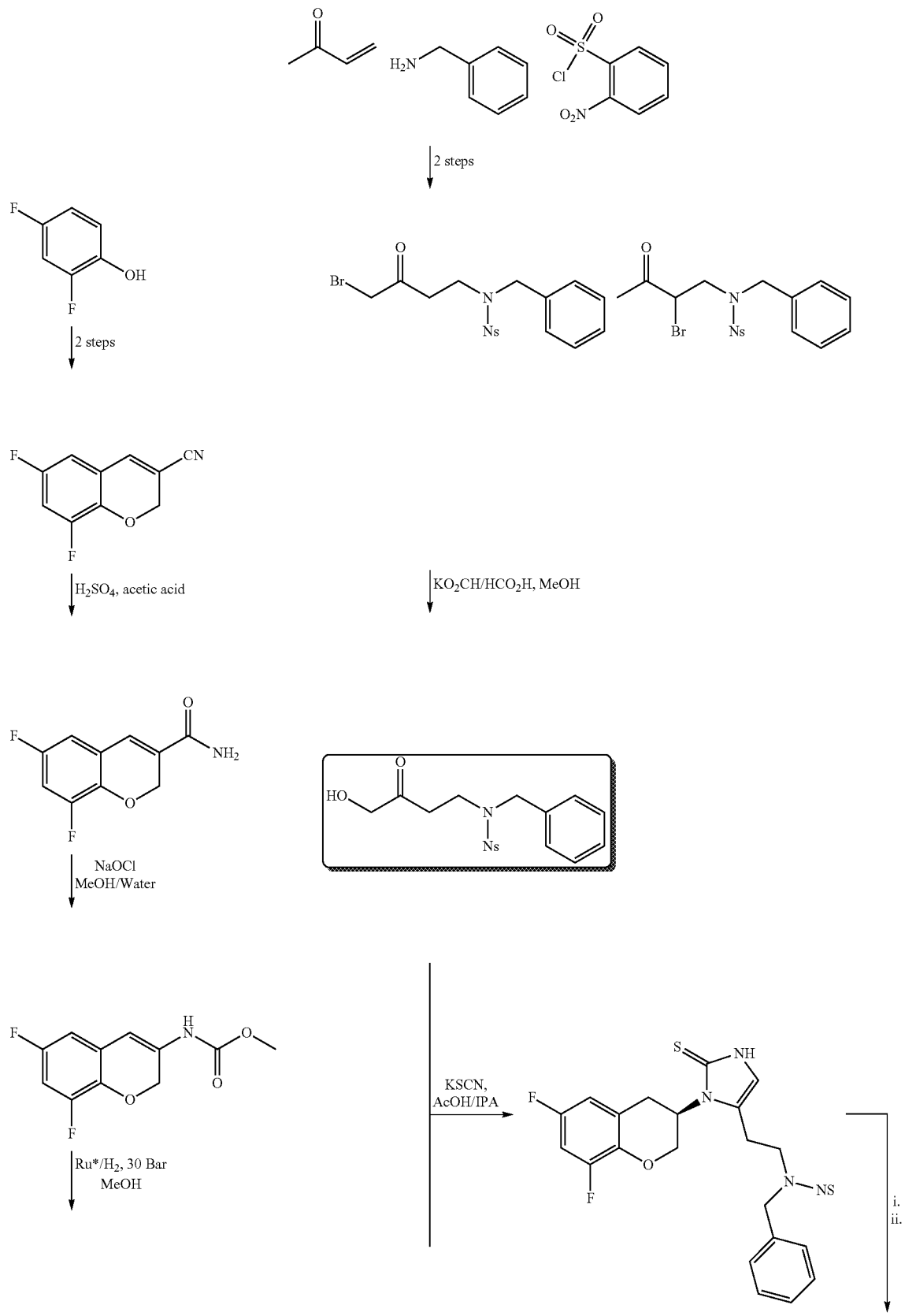

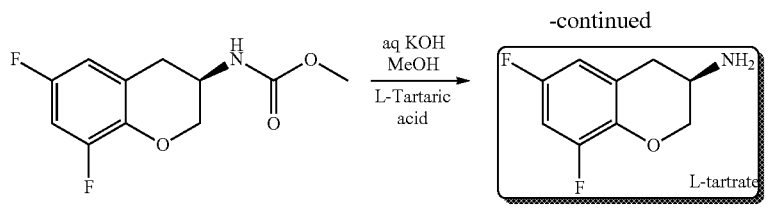

i. KOH, Thioglycolic acid or cysteine
ii. MEK

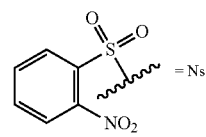  = Ns

In step (iii), the Ru-based catalyst may comprise a chiral bisphosphine ligand. The chiral bisphosphine ligand may be (R)-ToIBINAP, (S)-ToIBINAP, (R)-BINAP or (S)-BINAP. Alternatively, the ligand may be a chiral ligand having the formula below, wherein p is from 1 to 6, and Ar means aryl group.

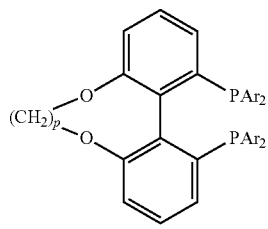

Such ligands and processes for their production are described in EP1214328A. Such ligands are from a series of ligands known under the name "TunePhos". The preferred TunePhos ligand is (R)-C3-TunePhos ligand which has the formula:

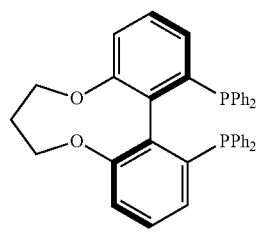

According to an aspect of the present invention, there is provided a compound of formula N prepared by a process disclosed herein. Preferably, the compound has the formula NA. More preferably, the compound has the formula R-NA.

According to an aspect of the present invention, there is provided the following 2-part synthetic route from the starting material 2,4-difluorophenol to (R)-5-(2-amino-ethyl)-1-(6,8-difluorochroman-3-yl)-1,3-dihydroimidazole-2-thione hydrochloride:

Part (1)

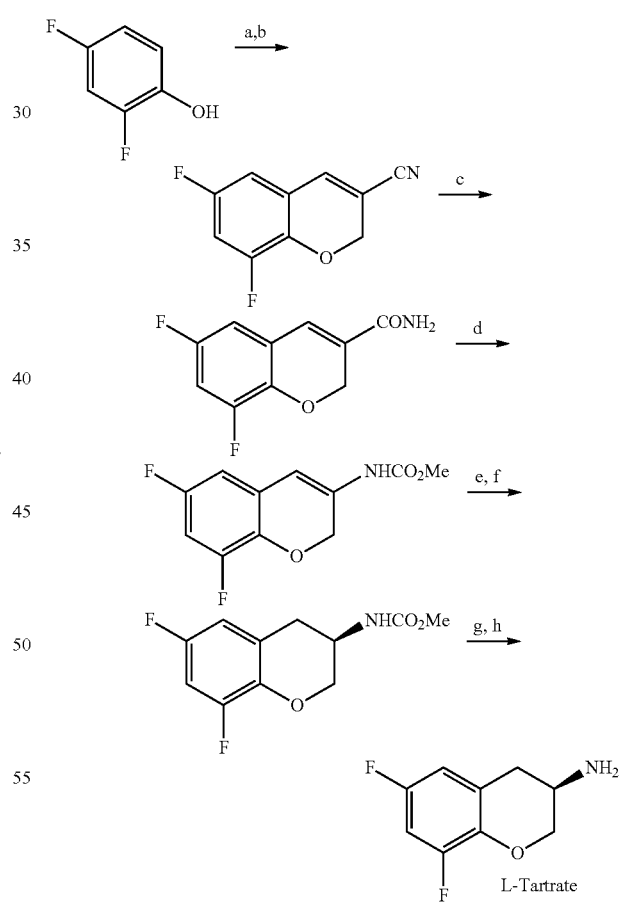

Preferred Reagents and Conditions:
a) HMTA, CF$_3$COOH, 115° C., 18 hours
b) CH$_2$CHCN, DABCO, DMF, water, 70° C., 16 hours
c) H$_2$SO$_4$, AcOH, 100° C., 1 hour
d) NaClO, NaOH, MeOH, 25° C., 24 hours e) (R)-C3-TunePhosRu(acac)₂ S/C 3000, 30 bar H₂, MeOH, 80° C., 20 hours
f) Water, 2-propanol, reflux to 20° C.
g) 40% KOH, MeOH, reflux, 24 hours
h) L-tartaric acid, ethanol, water, RT, 1 hour
   Part (2)

d') KOH, AcOH, reflux, 1 hour
e') HCl, water, 2-propanol, 75° C., 4 hours
f') KSCN, AcOH, 100° C., 2-4 hours
g') NaHCO₃, water, EtOH
h') NaBH₄, 2-propanol, THF, water, 20-25° C., 16 hours
i') HCl, 2-propanol, water, reflux, 1-2 hours

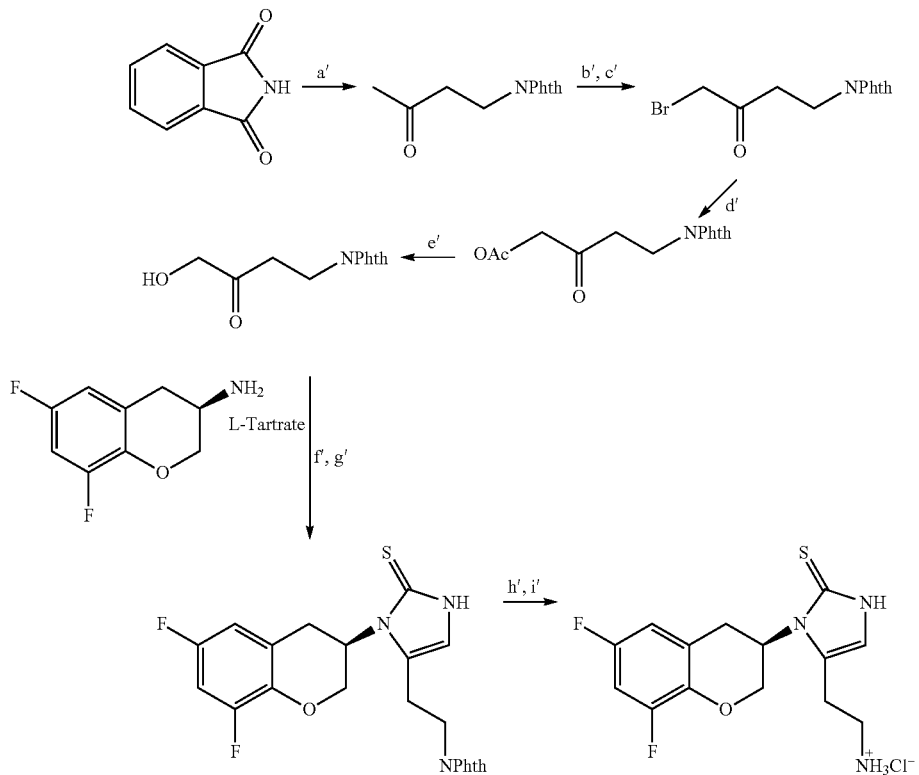

Preferred Reagents and Conditions
a') methyl vinyl ketone, t-BuONa, EtOAc, EtOH, 40-50° C., 2-3 hours
b') Br₂, MeOH, 20-25° C., 5 hours
c') water, reflux, 1 hour The (R)-5-(2-Aminoethyl)-1-(6,8-difluorochroman-3-yl)-1,3-dihydroimidazole-2-thione hydrochloride may then be used to prepare (R)-5-(2-(benzylamino)ethyl)-1-(6,8-difluorochroman-3-yl)-1H-imidazole-2(3H)-thione as follows.

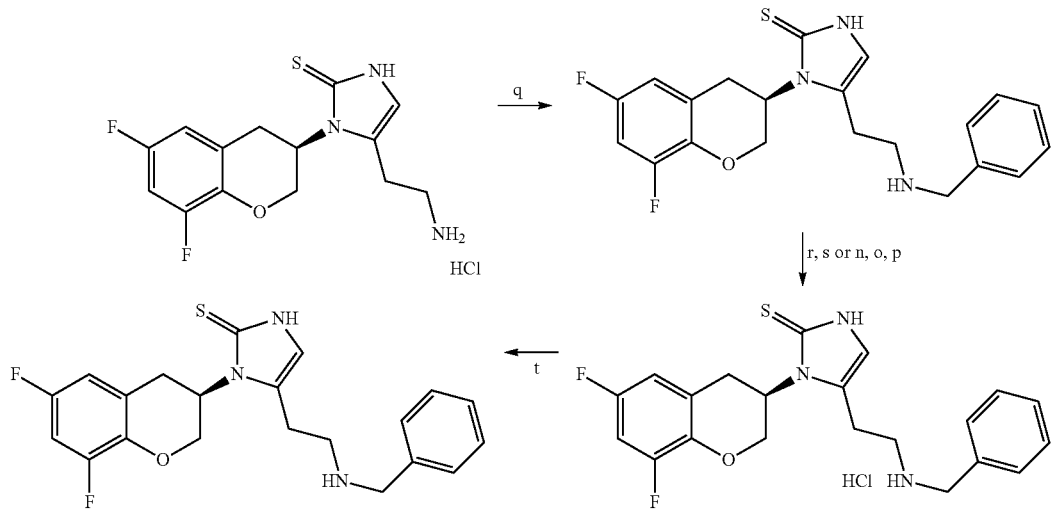

Preferred Reaction Conditions/Reagents:
q) NaBH(OAc)₃, PhCHO, IPA;
t) NaOH, MeOH, H₂O
  Either r) and s):
r) HCl aq;
s) MeOH/Toluene;
  Or n), o) and p):
n) HCl aq;
o) MeOH, toluene;
p) IPA.

According to an aspect of the present invention, there is provided a compound of formula MA prepared by a process disclosed herein.

According to an aspect of the present invention, there is provided a compound of formula Q or a salt thereof prepared by a process disclosed herein. Preferably, the compound has the formula QA. More preferably, the compound has the formula R-QA. Most preferably, there is provided the L-tartrate salt of the compound of formula R-QA prepared by a process disclosed herein.

According to an aspect of the present invention, there is provided a compound of formula Y or a salt thereof prepared by a process disclosed herein. Preferably, the compound is (R)-5-(2-(benzylamino)ethyl)-1-(6,8-difluorochroman-3-yl)-1H-imidazole-2(3H)-thione or (R)-5-(2-(benzylamino)ethyl)-1-(6,8-difluorochroman-3-yl)-1H-imidazole-2(3H)-thione hydrochloride. More preferably, the compound is (R)-5-(2-(benzylamino)ethyl)-1-(6,8-difluorochroman-3-yl)-1H-imidazole-2(3H)-thione.

According to an aspect of the present invention, there is provided a pharmaceutical composition comprising a therapeutically effective amount of a compound of formula E or Y or a salt thereof prepared by a process disclosed herein in combination with a pharmaceutically effective carrier.

According to an aspect of the present invention, there is provided a compound of formula E or Y or a salt thereof prepared by a process disclosed herein for use in inhibiting dopamine-β-hydroxylase.

According to an aspect of the present invention, there is provided a compound of formula E or Y or a salt thereof prepared by a process disclosed herein for use in treating cardiovascular disorders, hypertension or chronic heart failure.

According to an aspect of the present invention, there is provided the use of a compound of formula E or Y or a salt thereof prepared by a process disclosed herein in the manufacture of a medicament for use in inhibiting dopamine-β-hydroxylase.

According to an aspect of the present invention, there is provided the use of a compound of formula E or Y or a salt thereof prepared by a process disclosed herein in the manufacture of a medicament for use in treating cardiovascular disorders, hypertension or chronic heart failure.

According to an aspect of the present invention, there is provided a method of treating cardiovascular disorders comprising administering a therapeutically effective amount of a compound of formula E or Y or a salt thereof prepared by a process disclosed herein to a patient in need thereof.

According to an aspect of the present invention, there is provided a method of treating hypertension comprising administering a therapeutically effective amount of a compound of formula E or Y or a salt thereof prepared by a process disclosed herein to a patient in need thereof.

According to an aspect of the present invention, there is provided a method of treating chronic or congestive heart failure comprising administering a therapeutically effective amount of a compound of formula E or Y or a salt thereof prepared by a, process disclosed herein to a patient in need thereof.

According to an aspect of the present invention, there is provided a method of treating one or more of the following indications: angina, arrhythmias, and circulatory disorders such as Raynaud's phenomenon comprising administering a therapeutically effective amount of a compound of formula E or Y or a salt thereof prepared by a process disclosed herein to a patient in need thereof.

EXAMPLES

Example 1

Nitro Chromene Synthesis

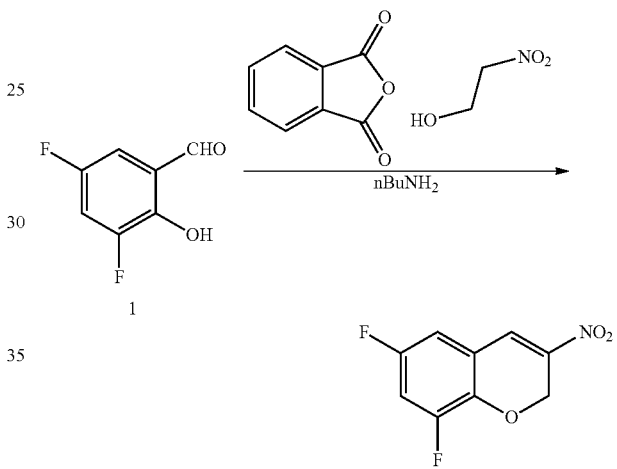

To 3,5-difluoro-2-hydroxybenzaldehyde (10 g, 63 mmol, 1 eq), di-n-butylamine (4.1 g, 32 mmol, 0.5 eq), phtalic anhydride (18.7 g, 126 mmol, 2 eq) in toluene (500 mL) was added nitroethanol (5.75 g, 63 mmol, 1 eq). The round bottomed flask fitted with a dean stark apparatus was refluxed for 18 h. The mixture was cooled and nitroethanol (5.75 g, 63 mmol, 1 eq) was added. The resulting reaction mixture was then reflux for 12 h. After cooling, the solution was evaporated down to approximately 150 mL and purified over silica gel (eluent ethyl acetate:hexane 1:1) this gave several fractions that contained only the product by TLC, these was evaporated under reduced pressure to yield 1.8 g which was 100% pure by HPLC area. Several more fractions were collected containing a mixture of product and starting material. These were combined and washed with 2% NaOH solution (2×50 mL) to remove starting material. The organic layer was washed with water (50 mL), dried over sodium sulfate and evaporated under reduced pressure to give 2.49 g of brown solid (100% pure by HPLC area). More fractions were collected. These were combined, washed with 2% NaOH solution (3×100 mL), water (100 mL) and dried over sodium sulfate. This was then filtered and evaporated down in vacuum to yield 6.14 g of a brown solid which was 91.3% pure by HPLC area. 6,8-difluoro-3-nitro-2H-chromene (9.90 g, 73.4%) was obtained as a brown solid.

Example 2

Nitro Chromene Synthesis with Column Purification

To a solution of isobenzofuran-1,3-dione (4.68 g, 31.6 mmol), 3,5-difluoro-2-hydroxybenzaldehyde (2.5 g, 15.81 mmol) in Toluene (25 ml) was added 2-nitroethanol (2.88 g, 31.6 mmol). The resulting mixture was heated to reflux overnight (Dean stark).

The reaction conversion was checked by TLC (eluent PE/EtOAc 9:1). A yellow spot was observed and corresponds to the expected product.

Reaction was cooled to room temperature and a plug of silica gel was performed. A pale brown solid (3.9 g) was obtained. $^1$H-NMR showed presence of product and starting material. The solid was dissolved in diethylether and the organic layer was washed with aqueous sodium carbonate, dried over $Na_2SO_4$, filtered and concentrated under reduced pressure. A pale brown solid (1.7 g,) was obtained. The $^1$H-NMR was indicated no starting material but still polymer from nitroethanol and residue of phtalic anhydride. A second silica plug (eluent: PE/EtOAc 95:5) was done. A pale yellow solid (1.5 g) was obtained. $^1$H-NMR of solid showed only product and polymer. The solid was recrystallized from methanol/water. A pale yellow solid (1.05 g, 31.2%) was obtained.

Example 3

Nitro Chromene Synthesis without Column Purification

To a solution of isobenzofuran-1,3-dione (18.74 g, 127 mmol), 3,5-difluoro-2-hydroxybenzaldehyde (10 g, 63.3 mmol) in Toluene (100 ml) was added 2-nitroethanol (6.86 ml, 95 mmol). The resulting mixture was heated to reflux for 24 h (Dean stark).

The reaction conversion was checked by HPLC and by $^1$H-NMR. Only 50% conversion was obtained.

The reaction mixture was cooled to room temperature and diluted with DCM (100 mL) and 1M NaOH solution (200 mL).

The biphasic system was stirred for 30 minutes and then separated (very difficult to see phase separation). The aqueous layer was washed with DCM (50 mL) and the combined organic layers were washed twice with water (2×50 ml), dried over sodium sulfate. The filtered organic layer was concentrated under reduced pressure. To the residue was added methanol (50 mL). The methanol was then removed by distillation under reduced pressure. A brown solution precipitated when most of the methanol was removed. More methanol was added and more solid crushed out then few drops of water was added to increase the product precipitation. The brown slurry was stirred for 30 minutes and filtered. The brown solid was washed with methanol/water (1:9, 5 mL) and dried in a vacuum oven at 40° C. for 12 h. 6,8-difluoro-3-nitro-2H-chromene (4.9 g, 22.99 mmol,) was obtained as brown solid in 36.3% yield.

HPLC showed a purity of 98% and $^1$H-NMR confirmed the structure and purity around 95%

Example 4

Reduction of Nitro Chromene to Nitro-alkane (Racemic Mixture)

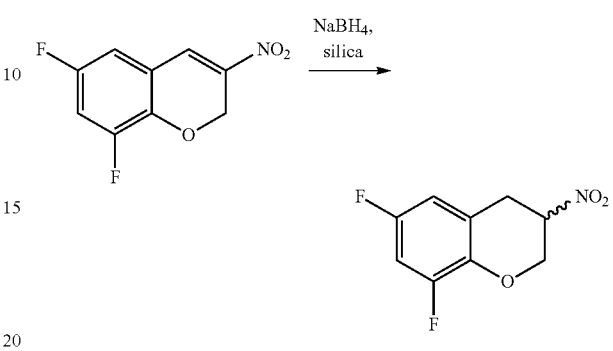

To a suspension of 6,8-difluoro-3-nitro-2H-chromene (213 mg, 0,999 mmol) and silica (0.8 g, 0,999 mmol) in a mixture of $CHCl_3$ (10 ml) and IPA (3.4 ml) at 0° C. was added portion wise sodium borohydride (95 mg, 2,498 mmol). The resulting mixture was stirred at 0° C. for 45 minutes. Reaction conversion was checked by HPLC. 1 mL of acetic acid was added at 0° C. and the resulting mixture was stirred for 30 minutes at room temperature. The slurry was filtered and the silica was washed with DCM. The filtrate was diluted with ethyl acetate and water and the biphasic system was separated. The aqueous layer was back extracted with ethyl acetate. The combined organic layers were washed with brine, dried over $MgSO_4$, filtered and concentrated under reduced pressure.

6,8-difluoro-3-nitrochroman (196 mg, 0,911 mmol, 91% yield) was obtained as a pale yellow oil.

Example 5

Preparation of 6,8-difluorochroman-3-one from nitro chromene

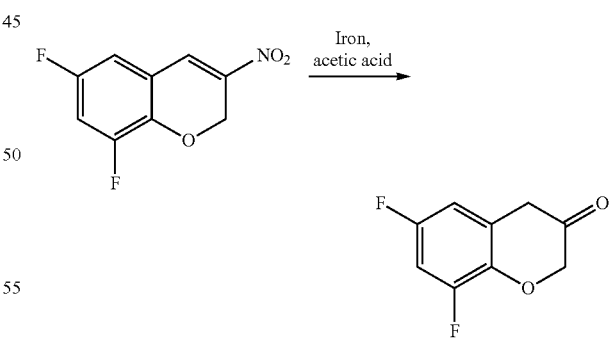

A solution of 6,8-difluoro-3-nitro-2H-chromene (100 mg, 0,469 mmol) in acetic acid (0.5 ml) is added slowly to a stirred slurry of iron (262 mg, 4.69 mmol) in acetic acid (1 ml) at 60deg. C. The reaction mixture is stirred at 60° C. for 2 hour then allowed to cool to room temperature and stirred overnight. The reaction mixture is poured onto ice-water (30 ml) and filtered through Celite. The solid was wash with dichloromethane (DCM) (50 ml). The organic portion is separated and washed with water (2×30 ml) and brine (30 ml), dried over MgSO$_4$, filtered and concentrated in vacuo to give a brown oil. 6,8-difluorochroman-3-one (75 mg, 0,407 mmol, 87% yield) was obtained as a brown oil.

Example 6

Preparation of 6,8-difluorochroman-3-one from methyl 6,8-difluoro-2H-chromen-3-yl-carbamate

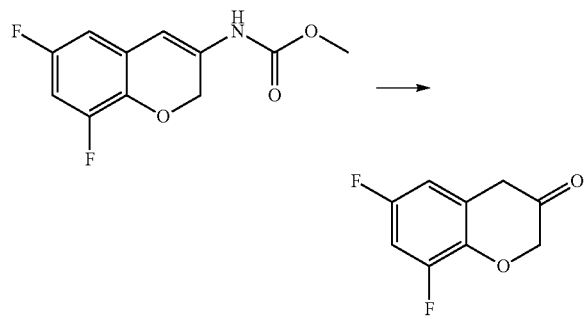

Methanol (1000 m ml) was added to a slurry of methyl 6,8-difluoro-2H-chromen-3-yl-carbamate (250 g, 1.037 mol) in hydrogen chloride 6N (2000 ml, 12 mol) at room temperature. The resulting mixture was reflux and stirred for 2 hours. Reaction monitored by HPLC.

Reaction was not complete but was stopped in order to avoid degradation of the product. The yellow solution was cooled to room temperature. A slurry (two type of solid) was observed and diluted with diethyl ether (300 mL). The resulting slurry was stirred at 5° C. for 1 hour then filtered. The yellow solid was washed with water. The resulting wet yellow solid was suspended in diethylether (400 mL) and petroleum ether (PE) (400 mL) was added. Slight yellow solid was stirred at room temperature overnight, filtered and washed with PE (300 mL), dried in a vacuum oven at 30° C. for 4 h. The wet sample was checked by NMR. No starting material was detected. A pale yellow solid (72.5 g, solid 1) was obtained. The mother liquors were concentrated to dryness. A yellow solid was obtained, suspended in diethyl ether and PE. The slurry was then stirred for 4 hours, filtered, washed with PE. A dark yellow solid (4.5 g, solid 2) was obtained. Solid 1 (2 g) was diluted in DCM and washed with water (pH=6). The organic layer was then dried over Na$_2$SO$_4$, filtered, concentrated to dryness. A crystalline pale yellow solid (1.9 g, solid 3) was obtained. NMR showed the same purity for solid 3 as for solid 1. The remaining part of solid 1 was then diluted in DCM. The resulting organic layer was washed with water, dried over Na$_2$SO$_4$, filtered and then concentrated to dryness. Slight yellow crystalline solid (68.5 g, solid 4) was obtained. NMR confirmed high quality material.

Loss on Drying (LOD): 1.03%.

Example 7

Biotransformation: Transaminases

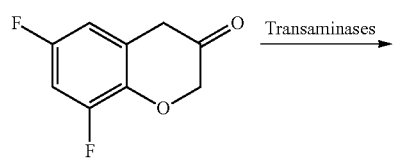

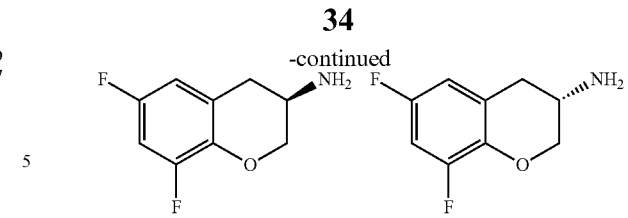

Codexis transaminases ATA-025, ATA-251 and ATA-P2-A07 recognized 6,8-difluorochroman-3-one as the substrate and produced the corresponding 6,8-difluorochroman-3-amine.

Experimental protocol

Preparation of triethanolamine buffer solution 200 mM (Solution 1):

Dissolve 14.9 g of triethanolamine in 500 mL of deionized water. Adjust pH to 7.5 by adding conc. HCl.

Preparation of 2.5M isopropylamine hydrochloride solution (Solution 2):

Dissolve 20.8 mL of conc. HCL in 40 mL. At 0° C., add isopropylamine (20.5 mL) drop wise over 1.5 hours and finally complete the volume to 100 mL with deionized water. The resulting pH is 4.

Preparation of PLP buffer solution (Solution 3, prepare in the day of experiment)

Dissolve 4.8 mg PLP in 20 mL of triethanolamine solution

General Protocol:

Weight 5 mg of each enzyme in a vial

Add 500 µL of PLP solution (Solution 3)

Add 400 µL of 2.5M iPrNH$_2$—HCl (Solution 2)

Add 15 mg of ketone

Add 190 µL of buffer (Solution 1)

Add 20 µL of DMSO

Stir the mixture overnight at 30° C.

400 µL of ethyl acetate was added to all the vials after overnight reaction. The biphasic system was stirred for 10 minutes and allowed to separate and TLC was done on organic layer. Eluent: Petroleum Ether/ethyl acetate 7:3 and DCM/MeOH 9:1.

Results

ATA-025: No starting material by TLC; produced (S)-6,8-difluorochroman-3-amine; Chiral HPLC: 72.8% ee.

ATA-251: No starting material by TLC; produced (R)-6,8-difluorochroman-3-amine; Chiral HPLC: 50% ee.

ATA-P2-A07: No starting material by TLC; produced (S)-6,8-difluorochroman-3-amine; Chiral HPLC: 99.0% ee.

Example 8

Solubility Study

The solubility of non-micronized and micronized (R)-5-(2-(benzylamino)ethyl)-1-(6,8-difluorochroman-3-yl)-1H-imidazole-2(3H)-thione in several organic solvents was determined.

Solubility Solubility was evaluated according to Eur. Ph. Chapter 5.11 at room temperature.

A comparison between the results obtained before and after micronization shows no overall significant changes in the solubility profile.

The following descriptions are used to describe the degree of solubility:

| Description | Approximate parts of solvent for one part of solute |
| --- | --- |
| Very soluble | less than 1 part |
| Freely soluble | from 1 to 10 parts |
| Soluble | from 10 to 30 parts |
| Sparingly soluble | from 30 to 100 parts |
| Slightly soluble | from 100 to 1000 parts |
| Very slightly soluble | from 1000 to 10,000 parts |
| Practically insoluble | greater than or equal to 10,000 parts |

The (R)-5-(2-(benzylamino)ethyl)-1-(6,8-difluorochroman-3-yl)-1H-imidazole-2(3H)-thione was soluble to some extent (mostly either sparingly soluble, slightly soluble or very slightly soluble) in most of the polar organic solvents tested. The (R)-5-(2-(benzylamino)ethyl)-1-(6,8-difluorochroman-3-yl)-1H-imidazole-2(3H)-thione was soluble to some extent (either sparingly soluble, slightly soluble or very slightly soluble) in all of the polar organic aprotic solvents tested.

The description of the solubilities of the non-micronized particles is shown below:

| Solvent | Description |
| --- | --- |
| 1,4-Dioxane | Slightly soluble |
| 2-propanol | Insoluble |
| Absolute ethanol | Practically insoluble |
| Acetone | Slightly soluble |
| Acetonitrile | Very slightly soluble |
| Chloroform | Very slightly soluble |
| Cyclohexane | Insoluble |
| Dichloromethane | Slightly soluble |
| Dimethylformamide | Sparingly soluble |
| DMSO | Sparingly soluble |
| Ethyl acetate | Very slightly soluble |
| Hexafluoroisopropanol | Sparingly soluble |
| Iso-octane (2,2,4-trimethylpentane) | Insoluble |
| Isopropyl acetate | Very slightly soluble |
| Methanol | Very slightly soluble |
| Methanol or acetonitrile acidified with 0.1% formic acid or TFA | Sparingly soluble |
| Methyl ethyl ketone | Slightly soluble |
| N,N-methylpirrolidone | Sparingly soluble |
| Tetrahydrofuran | Sparingly soluble |
| Toluene | Very slightly soluble |
| Trifluoroethanol | Slightly soluble |

The description of the solubilities of the micronized particles is shown below:

| Solvent | Description |
| --- | --- |
| 1,4-Dioxane | Very slightly soluble |
| 2-propanol | Insoluble |
| Absolute ethanol | Very slightly soluble |
| Acetone | Slightly soluble |
| Acetonitrile | Very slightly soluble |
| Chloroform | Slightly soluble |
| Cyclohexane | Insoluble |
| Dichloromethane | Very slightly soluble |
| Dimethylformamide | Sparingly soluble |
| DMSO | Slightly soluble |
| Ethyl acetate | Very slightly soluble |
| Iso-octane (2,2,4-trimethylpentane) | Practically insoluble |
| Methanol | Very slightly soluble |
| Methanol or acetonitrile acidified with 0.1% formic acid or TFA | Slightly soluble |
| Methyl ethyl ketone | Slightly soluble |
| N,N-methylpirrolidone | Sparingly soluble |
| Tetrahydrofuran | Sparingly soluble |

The aqueous solubility of (R)-5-(2-(benzylamino)ethyl)-1-(6,8-difluorochroman-3-yl)-1H-imidazole-2(3H)-thione was determined in triplicate at 37° C. Aqueous solutions of HCl (pH 1.2, 2.0, 3.0), potassium chloride (pH 1.2, 2.0), acid phthalate (pH 3.0), acetate (pH 4.5, 5.5), phosphate (pH 7.4) and boric acid (pH 9.0) were tested. It was seen that the solubility of (R)-5-(2-(benzylamino)ethyl)-1-(6,8-difluorochroman-3-yl)-1H-imidazole-2(3H)-thione (both non-micronized and micronized) decreases with the increase of pH. Maximum solubility was achieved by using HCl 0.01 (pH 2.0); further increase in pH resulted in solubility decrease. There was no considerable improvement in solubility after micronization. In fact, solubility in HCl 0.01 (pH 2.0) is lower.

Example 9

Particle Size Study

The particle size distribution of (R)-5-(2-(benzylamino)ethyl)-1-(6,8-difluorochroman-3-yl)-1H-imidazole-2(3H)-thione was determined by laser diffraction.

Particle size determination experiments were performed in a Malvern Mastersizer 2000 laser difractometer equipped with a wet dispersion unit Hydro 2000S. The analytical information obtained was acquired and processed with the software Malvern Mastersizer 5.54.

The following instrumental settings were used:

| Equipment | Malvern Mastersizer 2000 | |
| --- | --- | --- |
| Material | Sample | (R) -5-(2-(benzylamino)ethyl)-1-(6,8-difluorochroman-3-yl)-1H- imidazole-2(3H)-thione |
| | Dispersant | Cyclohexane with surfactant; refractive index 1.426 |
| Measurement | Background time | 15 seconds |
| | Measurement time | 30 seconds |
| | Pump/Stirrer speed | 2500 rpm |
| | Dispersant level threshold | 15% |

The results are summarised below.

The particle size distribution was measured on samples both before micronization and after micronization.

A volume weighted distribution was obtained for the samples. The contribution of each particle in the distribution relates to the volume of that particle, i.e. the relative contribution will be proportional to $(size)^3$.

The parameters $(D_vX)$ are reported below based on the maximum particle size for a given percentage volume of the sample. In DOC, D stands for diameter, v indicates a volume distribution weighting, and X is the percentage of sample below this particle size. For example, the $D_v50$ would be the maximum particle diameter below which 50% of the sample volume exists.

Three samples of non-micronized particles of (R)-5-(2-(benzylamino)ethyl)-1-(6,8-difluorochroman-3-yl)-1H-imidazole-2(3H)-thione were tested.

The D$_v$10 figure for the samples ranges from around 30 µm to around 150 µm.

The D$_v$50 figure for the samples ranges from around 200 µm to around 300 µm.

The D$_v$90 figure ranges from around 400 µm to around 600 µm.

Nine samples of one micronized batch of (R)-5-(2-(benzylamino)ethyl)-1-(6,8-difluorochroman-3-yl)-1H-imidazole-2(3H)-thione were tested.

The D$_v$10 figure for the samples ranges from around 3 µm to around 8 µm.

The D$_v$50 figure for the samples ranges from around 20 µm to around 50 µm.

The D$_v$90 figure ranges from around 100 µm to around 350 µm.

It will be appreciated that the invention may be modified within the scope of the appended claims.

The invention claimed is:

1. A process for preparing the (R)-enantiomer (R-N) or the (S)-enantiomer (S-N), the process comprising subjecting a compound of formula M to reduction using a reductase enzyme, wherein: X is CH$_2$, oxygen or sulphur; and one of R$_1$, R$_2$ and R$_3$ is hydrogen and the others are fluorine:

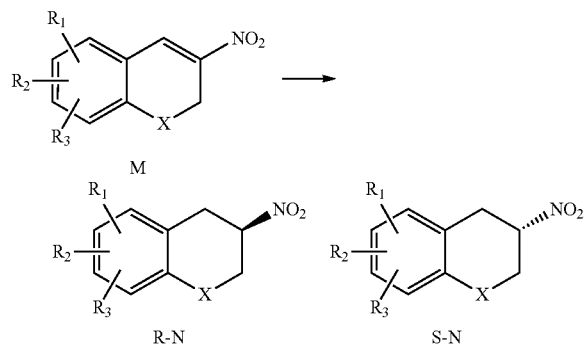

2. The process of claim 1, wherein the compound M has the formula MB, the process further comprising reacting a compound of formula R with 2-nitroethanol or nitroethylene to obtain the compound MB:

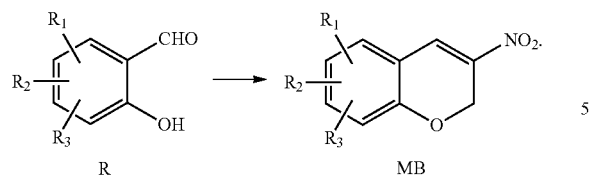

3. The process according to claim 2, wherein the compound R has the formula RA, comprising reacting a compound of formula RA to form a compound of formula MA:

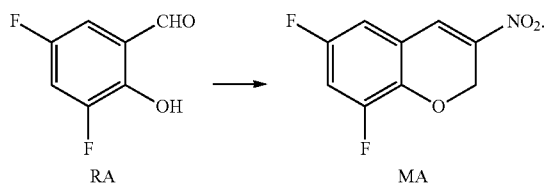

4. The process according to claim 1, wherein compound M has the formula MA:

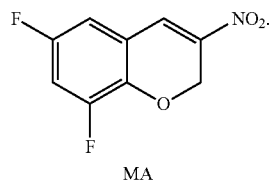

5. The process according to claim 1, wherein the enantiomer of the compound formula N is converted to the corresponding enantiomer of the compound of formula Q, or a salt thereof, by hydrogenation:

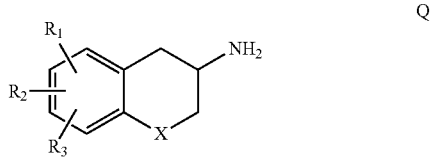

wherein: X is CH$_2$, oxygen or sulphur; and one of R$_1$, R$_2$ and R$_3$ is hydrogen and the others are fluorine.

6. The process according to claim 1, wherein the compound R-N has the formula R-NA and the method of converting the compound R-NA to the (R)-enantiomer of compound Q, which has the formula R-QA or a salt thereof:

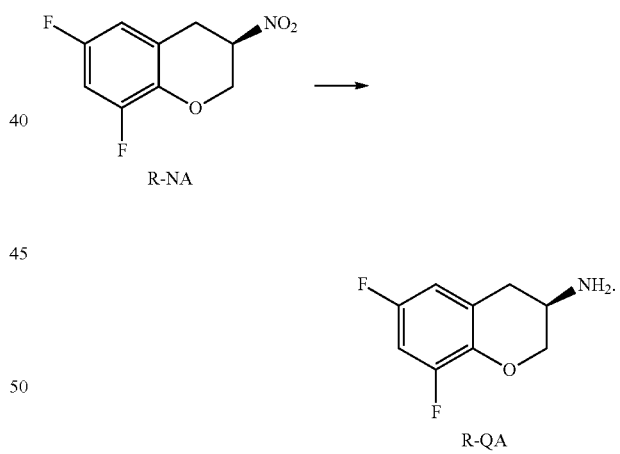

7. The process according to claim 6, wherein the compound of formula R-QA is converted to the L-tartrate salt thereof.

8. The process according to claim 5, wherein the hydrogenation comprises the use of hydrazine hydrate and Raney-Nickel; the use of Raney-Nickel under a hydrogen atmosphere; the use of palladium under a hydrogen atmosphere; or the use of palladium and formic acid, ammonium formate, or hydrazine hydrate.

9. The process of claim 5, further comprising preparing the (R)- or (S)-enantiomer of a compound of formula E or a salt thereof,

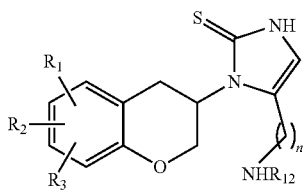

E the process comprising reacting the corresponding (R)-(S)-enantiomer of the compound of formula Q as defined in claim 5 with a compound of formula D2 with a water soluble thiocyanate salt in the presence of an organic acid in a substantially inert solvent,

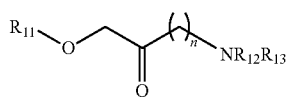

D2 wherein n signifies 1, 2 or 3, $R_{12}$ signifies hydrogen, alkyl or alkylaryl group, $R_{11}$ signifies a hydroxyl protecting group and $R_{13}$ signifies an amino protecting group, or $R_{11}$ is defined as above but $R_{12}$ and $R_{13}$ taken together represent a phthalimido group;

followed by subsequent deprotection of the intermediate products F to I:

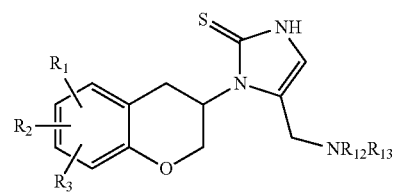

F

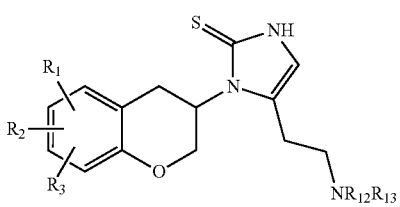

G

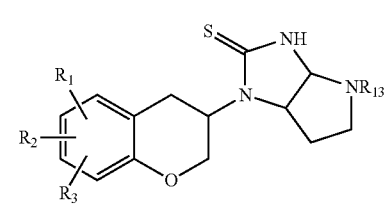

H

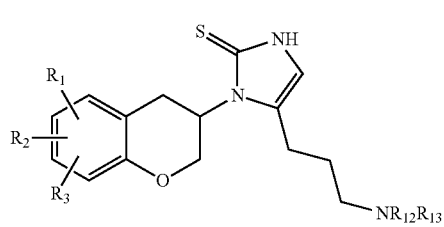

I to produce the respective (R)- or (S)-enantiomer of the compound of formula E or salt thereof.

10. The process according to claim 9, wherein the compound E is
(R)-5-(2-aminoethyl)-1(6,8-difluorochroman-3-yl)-1,3-dihydroimidazole-2-thione or (R)-5-(2-aminoethyl)-1-(6,8-difluorochroman-3-yl)-1,3-dihydroimidazole-2-thione hydrochloride.

11. The process according to claim 9, wherein the compound E is
(S1-5-(2-aminoethyl)-1-(5,7-difluoro-1,2,3,4-tetrahydronaphthalen-2-yl)-1,3-dihydroimidazole-2-thione;
(R)-5-(2-aminoethyl)-1-(6,7-difluorochroman-3-yl)-1,3-dihydrohnidazole-2-thione;
(S)-5-(2-aminoethyl)-1-(6,8-difluorochroman-3-yl)-1,3-dihydroimidazole-2-thione;
(R)-5-aminomethyl-1-(6,8-difluorochroman-3-yl)-1,3-dihydroimidazole-2-thione;
(R)-5-(3-aminopropyl)-1-(6,8-difluoroehroman-3-yl)-1,3-dihydroimidazole-2-thione;
(S)-5-(3-aminopropyl)-1-(5,7-difluoro-1,2,3,4-tetrahydronaphthalen-2-yl)-1,3-dihydroimidazole-2-thione; or
(R)-1-(6,8-difluorochroman-3-yl)-5-(2-methylaminoethyl)-1,3-dihydroimidazole-2-thione or a salt thereof.

12. The process according to claim 11, wherein the salt is the hydrochloride salt.

13. The process of claim 9, further comprising preparing the individual (R)- or (S)-enantiomer or a mixture of the (R)- and (S)-enantiomers or a pharmaceutically acceptable salt of a compound of formula Y, which process comprises reacting the (R)- or (S)-enantiomer or a mixture of the (R)- and (S)-enantiomers of a compound of Formula E with a compound of formula IX under reductive alkylation conditions,

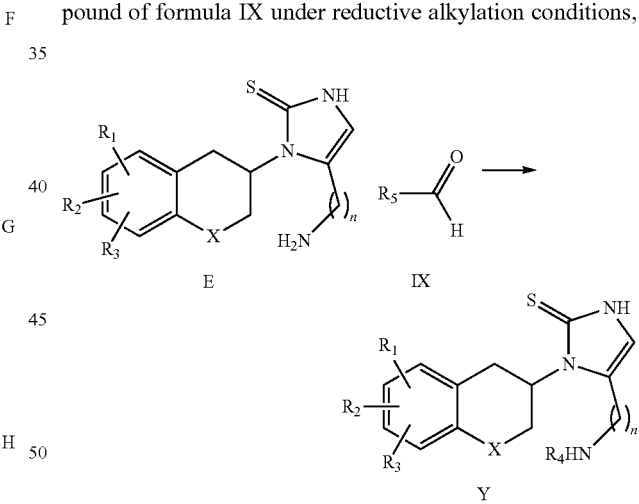

wherein X is $CH_2$, oxygen or sulphur; and one of $R_1$, $R_2$ and $R_3$ is hydrogen and the others are fluorine; $R_4$ signifies -alkyl-aryl or -alkyl-heteroaryl; $R_5$ signifies aryl or heteroaryl, n is 2 or 3; wherein the term alkyl means hydrocarbon chains, straight or branched, containing from one to six carbon atoms, optionally substituted by aryl, alkoxy, halogen, alkoxycarbonyl or hydroxycarbonyl groups; the term aryl means a phenyl or naphthyl group, optionally substituted by alkyl, alkyloxy, halogen or nitro group; the term halogen means fluorine, chlorine, bromine or iodine; the term heteroaryl means heteroaromatic group.

14. The process according to claim 13, wherein the compound of formula Y is a compound of formula X:

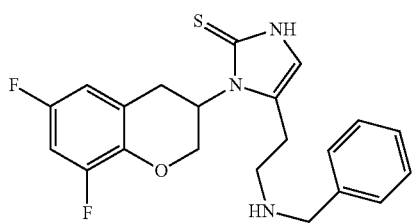

its (R)- or (S)-enantiomer, or mixture of the (R)- and (S)-enantiomer, or a pharmaceutically acceptable salt thereof.

15. The process according to claim 14, wherein the compound is the (R)-enantiomer of the compound of Formula X.

16. The process according to claim 14, comprising the hydrochloride salt of the compound of formula X.

17. The process of claim 5, further comprising preparing the (R)-enantiomer or a pharmaceutically acceptable salt of a compound of formula YA (R-YA), which wherein process comprises reacting a salt of the (R)-enantiomer of the compound of formula QA (R-QA) with a compound of formula C, to obtain a compound of formula V and converting the compound of formula V to the compound of formula R-YA:

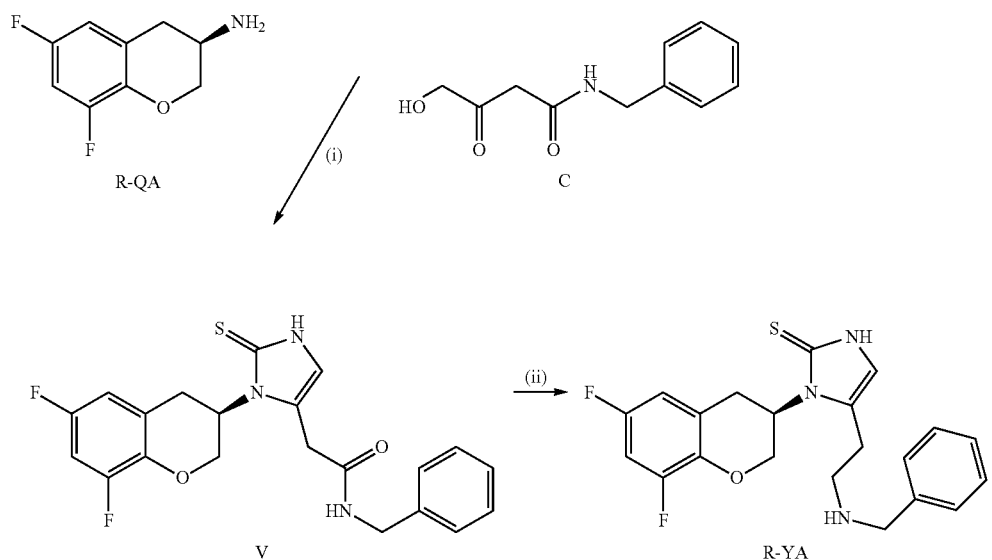

wherein the salt of compound R-QA is selected from L-tartrate, hydrochloride, mesylate, tosylate, trifluoroacetate, citrate, glycolate and oxalate.

18. The process according to claim 17, wherein the salt of compound R-QA is the L-tartrate salt.

19. The process of claim 5, further comprising preparing the (R)-enantiomer or a pharmaceutically acceptable salt thereof of a compound of formula YA (R-YA), which process comprises reacting a salt of the (R)-enantiomer of the compound of Formula QA (R-QA) with a compound of formula VI, to obtain a compound of formula VII and converting the compound of formula VII to the compound of formula R-YA:

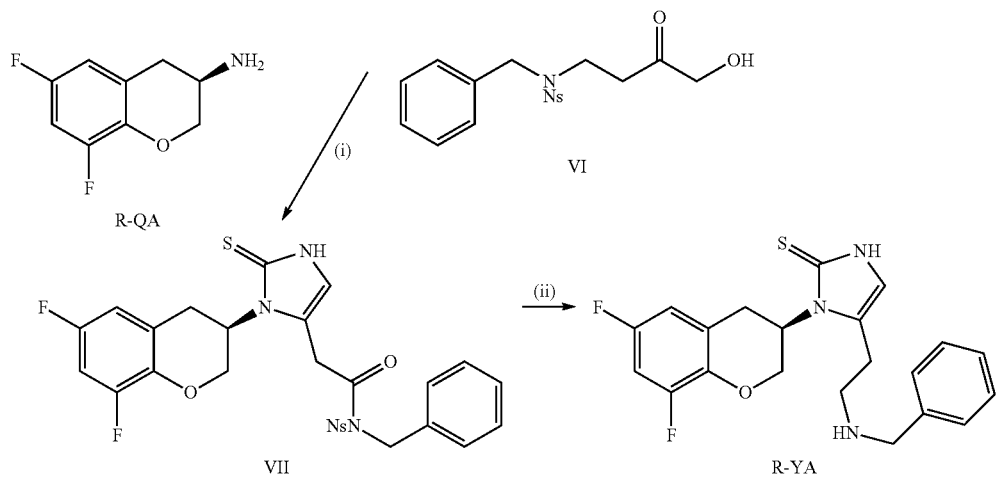

wherein Ns signifies o-nitrophenylsulphonyl and the salt of compound R-QA is selected from L-tartrate, hydrochloride, mesylate, tosylate, trifluoroacetate, citrate, glycolate and oxalate.

20. The process according to claim 19, wherein the salt of compound R-QA is the L-tartrate salt.

* * * * *

UNITED STATES PATENT AND TRADEMARK OFFICE
CERTIFICATE OF CORRECTION

PATENT NO. : 10,329,268 B2
APPLICATION NO. : 15/021605
DATED : June 25, 2019
INVENTOR(S) : Domenico Russo et al.

It is certified that error appears in the above-identified patent and that said Letters Patent is hereby corrected as shown below:

In the Claims

Claim 5, Column 38, Line 15, replace "compound formula N" with --compound of formula N--.

Claim 9, Column 39, Lines 12-13, replace "(R)- (S)-enantiomer of" with --(R)-or (S)-enantiomer of--.

Claim 10, Column 40, Lines 5-6, replace "(R)-5-(2-aminoethyl)-1(6,8-difluorochroman-3-yl)" with --(R)-5-(2-aminoethyl)-1-(6,8-difluorochroman-3-yl)--.

Claim 11, Column 40, Line 11, replace "(S1-5-(2-aminoethyl)" with --(S)-5-(2-aminoethyl)--.

Claim 11, Column 40, Line 14, replace "dihydrohnidazole-2-thione;" with --dihydroimidazole-2-thione--.

Claim 11, Column 40, Line 19, replace "(6,8-difluoroehroman-3-yl)" with --(6,8-difluorochroman-3-yl)--.

Claim 17, Column 42, Line 8, replace "YA (R-YA), which wherein process" with --YA (R-YA), wherein process--.

Signed and Sealed this
Eleventh Day of February, 2020

Andrei Iancu
*Director of the United States Patent and Trademark Office*